(12) United States Patent
Owen et al.

(10) Patent No.: US 8,586,541 B2
(45) Date of Patent: *Nov. 19, 2013

(54) POLYMERIC BIOSURFACTANTS

(75) Inventors: Donald Owen, Madisonville, LA (US); Lili Fan, Kenner, LA (US)

(73) Assignee: Therapeutic Peptides, Inc., Baton Rouge, LA (US)

( * ) Notice: Subject to any disclaimer, the term of this patent is extended or adjusted under 35 U.S.C. 154(b) by 1034 days.

This patent is subject to a terminal disclaimer.

(21) Appl. No.: 12/227,825

(22) PCT Filed: May 31, 2007

(86) PCT No.: PCT/US2007/012799
§ 371 (c)(1), (2), (4) Date: Aug. 17, 2009

(87) PCT Pub. No.: WO2007/143006
PCT Pub. Date: Dec. 13, 2007

(65) Prior Publication Data
US 2010/0144643 A1 Jun. 10, 2010

Related U.S. Application Data

(60) Provisional application No. 60/809,825, filed on Jun. 1, 2006.

(51) Int. Cl.
*A61K 8/64* (2006.01)
*A61Q 19/00* (2006.01)
*C07K 5/10* (2006.01)
*C07K 7/06* (2006.01)

(52) U.S. Cl.
USPC ......................................... 514/18.8; 530/330

(58) Field of Classification Search
None
See application file for complete search history.

(56) References Cited

U.S. PATENT DOCUMENTS 5,725,864 A * 3/1998 Yamamoto et al. ........ 424/278.1

OTHER PUBLICATIONS

Brown, M.J. Biosurfactants for cosmetic applications. International Journal of Cosmetic Science, 1991, 13, pp. 61-64.*

* cited by examiner

*Primary Examiner* — Robert A Wax
*Assistant Examiner* — Jessica Worsham
(74) *Attorney, Agent, or Firm* — Louis C. Paul

(57) ABSTRACT

The present invention is directed to biosurfactants that can self-assemble or auto-aggregate into polymeric micellar structures and their use in topically-applied dermatologic products. The invention relates in particular to polymeric acylated biosurfactants (PABs) conforming to the formula Acyl-AA-Term where Acyl is an 8- to 22-membered carbon chain, branched or unbranched, saturated or unsaturated, AA is a consecutive sequence of four to nine amino acid residues, where at least one, preferably at least two of the amino acid residues is charged, and Term is an acid C-terminus or an amide C-terminus. PABs of the present invention have low critical micelle concentrations (predominantly less than about 100 ppm) in an aqueous environment of Minimal Essential Media (MEM) and can lower the surface tension in the aqueous MEM environment to less about 50 dynes/cm2. They also have the ability to increase metabolic soluble proteins.

7 Claims, No Drawings

SEQUENCE LISTING

```
<160> NUMBER OF SEQ ID NOS: 33

<210> SEQ ID NO 1
<211> LENGTH: 4
<212> TYPE: PRT
<213> ORGANISM: Artificial Sequence
<220> FEATURE:
<223> OTHER INFORMATION: Synthetic peptide sequence
<220> FEATURE:
<221> NAME/KEY: MISC_FEATURE
<222> LOCATION: (1)..(1)
<223> OTHER INFORMATION: Myristolated
```

```
<220> FEATURE:
<221> NAME/KEY: MISC_FEATURE
<222> LOCATION: (4)..(4)
<223> OTHER INFORMATION: amide-terminated amino acid

<400> SEQUENCE: 1

Lys Ala Lys Ala
1

<210> SEQ ID NO 2
<211> LENGTH: 4
<212> TYPE: PRT
<213> ORGANISM: Artificial Sequence
<220> FEATURE:
<223> OTHER INFORMATION: Synthetic peptide sequence
<220> FEATURE:
<221> NAME/KEY: MISC_FEATURE
<222> LOCATION: (1)..(1)
<223> OTHER INFORMATION: Myristoylated
<220> FEATURE:
<221> NAME/KEY: MISC_FEATURE
<222> LOCATION: (4)..(4)
<223> OTHER INFORMATION: amide-terminated amino acid

<400> SEQUENCE: 2

Ala Lys Ala Lys
1

<210> SEQ ID NO 3
<211> LENGTH: 4
<212> TYPE: PRT
<213> ORGANISM: Artificial Sequence
<220> FEATURE:
<223> OTHER INFORMATION: Synthetic peptide sequence
<220> FEATURE:
<221> NAME/KEY: MISC_FEATURE
<222> LOCATION: (1)..(1)
<223> OTHER INFORMATION: Palmitoylated
<220> FEATURE:
<221> NAME/KEY: MISC_FEATURE
<222> LOCATION: (4)..(4)
<223> OTHER INFORMATION: amide-terminated amino acid

<400> SEQUENCE: 3

Gly Arg Lys Gly
1

<210> SEQ ID NO 4
<211> LENGTH: 4
<212> TYPE: PRT
<213> ORGANISM: Artificial Sequence
<220> FEATURE:
<223> OTHER INFORMATION: Synthetic peptide sequence
<220> FEATURE:
<221> NAME/KEY: MISC_FEATURE
<222> LOCATION: (1)..(1)
<223> OTHER INFORMATION: Myristoylated
<220> FEATURE:
<221> NAME/KEY: MISC_FEATURE
<222> LOCATION: (4)..(4)
<223> OTHER INFORMATION: amide-terminated amino acid

<400> SEQUENCE: 4

Gly Arg Lys Gly
1

<210> SEQ ID NO 5
<211> LENGTH: 4
<212> TYPE: PRT
<213> ORGANISM: Artificial Sequence
<220> FEATURE:
<223> OTHER INFORMATION: Synthetic peptide sequence
```

```
<220> FEATURE:
<221> NAME/KEY: MISC_FEATURE
<222> LOCATION: (1)..(1)
<223> OTHER INFORMATION: Myristoylated
<220> FEATURE:
<221> NAME/KEY: MISC_FEATURE
<222> LOCATION: (4)..(4)
<223> OTHER INFORMATION: amide-terminated amino acid

<400> SEQUENCE: 5

Leu Ala Lys Lys
1

<210> SEQ ID NO 6
<211> LENGTH: 4
<212> TYPE: PRT
<213> ORGANISM: Artificial Sequence
<220> FEATURE:
<223> OTHER INFORMATION: Synthetic peptide sequence
<220> FEATURE:
<221> NAME/KEY: MISC_FEATURE
<222> LOCATION: (1)..(1)
<223> OTHER INFORMATION: Palmitoylated
<220> FEATURE:
<221> NAME/KEY: MISC_FEATURE
<222> LOCATION: (4)..(4)
<223> OTHER INFORMATION: amide-terminated amino acid

<400> SEQUENCE: 6

Gly Gln Pro Arg
1

<210> SEQ ID NO 7
<211> LENGTH: 5
<212> TYPE: PRT
<213> ORGANISM: Artificial Sequence
<220> FEATURE:
<223> OTHER INFORMATION: Myristoylated, amide-terminated synthetic amino
      acid sequence
<220> FEATURE:
<221> NAME/KEY: MISC_FEATURE
<222> LOCATION: (1)..(1)
<223> OTHER INFORMATION: Myristoylated
<220> FEATURE:
<221> NAME/KEY: MISC_FEATURE
<222> LOCATION: (5)..(5)
<223> OTHER INFORMATION: amide-terminated amino acid

<400> SEQUENCE: 7

Lys Leu Ala Lys Lys
1               5

<210> SEQ ID NO 8
<211> LENGTH: 5
<212> TYPE: PRT
<213> ORGANISM: Artificial Sequence
<220> FEATURE:
<223> OTHER INFORMATION: Synthetic peptide sequence
<220> FEATURE:
<221> NAME/KEY: MISC_FEATURE
<222> LOCATION: (1)..(1)
<223> OTHER INFORMATION: Palmitoylated

<400> SEQUENCE: 8

Lys Leu Ala Lys Lys
1               5

<210> SEQ ID NO 9
<211> LENGTH: 5
<212> TYPE: PRT
<213> ORGANISM: Artificial Sequence
<220> FEATURE:
```

```
<223> OTHER INFORMATION: Synthetic peptide sequence
<220> FEATURE:
<221> NAME/KEY: MISC_FEATURE
<222> LOCATION: (1)..(1)
<223> OTHER INFORMATION: Myristoylated
<220> FEATURE:
<221> NAME/KEY: MISC_FEATURE
<222> LOCATION: (5)..(5)
<223> OTHER INFORMATION: amide-terminated amino acid

<400> SEQUENCE: 9

Lys Lys Gly Glu Met
1               5

<210> SEQ ID NO 10
<211> LENGTH: 5
<212> TYPE: PRT
<213> ORGANISM: Artificial Sequence
<220> FEATURE:
<223> OTHER INFORMATION: Synthetic peptide sequence
<220> FEATURE:
<221> NAME/KEY: MISC_FEATURE
<222> LOCATION: (1)..(1)
<223> OTHER INFORMATION: Myristoylated
<220> FEATURE:
<221> NAME/KEY: MISC_FEATURE
<222> LOCATION: (5)..(5)
<223> OTHER INFORMATION: amide-terminated amino acid

<400> SEQUENCE: 10

Lys Arg Gly Lys Pro
1               5

<210> SEQ ID NO 11
<211> LENGTH: 5
<212> TYPE: PRT
<213> ORGANISM: Artificial Sequence
<220> FEATURE:
<223> OTHER INFORMATION: Synthetic peptide sequence
<220> FEATURE:
<221> NAME/KEY: MISC_FEATURE
<222> LOCATION: (1)..(1)
<223> OTHER INFORMATION: Palmitoylated

<400> SEQUENCE: 11

Lys Arg Gly Asp Arg
1               5

<210> SEQ ID NO 12
<211> LENGTH: 5
<212> TYPE: PRT
<213> ORGANISM: Artificial Sequence
<220> FEATURE:
<223> OTHER INFORMATION: Synthetic peptide sequence
<220> FEATURE:
<221> NAME/KEY: MISC_FEATURE
<222> LOCATION: (1)..(1)
<223> OTHER INFORMATION: Myristoylated
<220> FEATURE:
<221> NAME/KEY: MISC_FEATURE
<222> LOCATION: (5)..(5)
<223> OTHER INFORMATION: amide-terminated amino acid

<400> SEQUENCE: 12

Lys Lys Ala Leu Lys
1               5

<210> SEQ ID NO 13
<211> LENGTH: 5
<212> TYPE: PRT
<213> ORGANISM: Artificial Sequence
<220> FEATURE:
```

<223> OTHER INFORMATION: Synthetic peptide sequence
<220> FEATURE:
<221> NAME/KEY: MISC_FEATURE
<222> LOCATION: (1)..(1)
<223> OTHER INFORMATION: Palmitoylated
<220> FEATURE:
<221> NAME/KEY: MISC_FEATURE
<222> LOCATION: (5)..(5)
<223> OTHER INFORMATION: amide-terminated amino acid

<400> SEQUENCE: 13

Lys Lys Ala Leu Lys
1               5

<210> SEQ ID NO 14
<211> LENGTH: 5
<212> TYPE: PRT
<213> ORGANISM: Artificial Sequence
<220> FEATURE:
<223> OTHER INFORMATION: Synthetic peptide sequence
<220> FEATURE:
<221> NAME/KEY: MISC_FEATURE
<222> LOCATION: (1)..(1)
<223> OTHER INFORMATION: Palmitoylated

<400> SEQUENCE: 14

Lys Lys Ala Leu Lys
1               5

<210> SEQ ID NO 15
<211> LENGTH: 5
<212> TYPE: PRT
<213> ORGANISM: Artificial sequence
<220> FEATURE:
<223> OTHER INFORMATION: Synthetic peptide sequence
<220> FEATURE:
<221> NAME/KEY: MISC_FEATURE
<222> LOCATION: (1)..(1)
<223> OTHER INFORMATION: Myristoylated
<220> FEATURE:
<221> NAME/KEY: MISC_FEATURE
<222> LOCATION: (5)..(5)
<223> OTHER INFORMATION: amide-terminated amino acid

<400> SEQUENCE: 15

Lys Lys Leu Ala Lys
1               5

<210> SEQ ID NO 16
<211> LENGTH: 5
<212> TYPE: PRT
<213> ORGANISM: Artificial sequence
<220> FEATURE:
<223> OTHER INFORMATION: Synthetic peptide sequence
<220> FEATURE:
<221> NAME/KEY: MISC_FEATURE
<222> LOCATION: (1)..(1)
<223> OTHER INFORMATION: Palmitoylated

<400> SEQUENCE: 16

Gly Arg Lys Gly Asp
1               5

<210> SEQ ID NO 17
<211> LENGTH: 5
<212> TYPE: PRT
<213> ORGANISM: Artificial sequence
<220> FEATURE:
<223> OTHER INFORMATION: Synthetic peptide sequence
<220> FEATURE:
<221> NAME/KEY: MISC_FEATURE
<222> LOCATION: (1)..(1)

```
<223> OTHER INFORMATION: Myristoylated
<220> FEATURE:
<221> NAME/KEY: MISC_FEATURE
<222> LOCATION: (5)..(5)
<223> OTHER INFORMATION: amide-terminated amino acid

<400> SEQUENCE: 17

Gly Arg Lys Gly Asp
1               5

<210> SEQ ID NO 18
<211> LENGTH: 6
<212> TYPE: PRT
<213> ORGANISM: Artificial sequence
<220> FEATURE:
<223> OTHER INFORMATION: Synthetic peptide sequence
<220> FEATURE:
<221> NAME/KEY: MISC_FEATURE
<222> LOCATION: (1)..(1)
<223> OTHER INFORMATION: Myristoylated

<400> SEQUENCE: 18

Lys Leu Ala Lys Lys Leu
1               5

<210> SEQ ID NO 19
<211> LENGTH: 6
<212> TYPE: PRT
<213> ORGANISM: Artificial sequence
<220> FEATURE:
<223> OTHER INFORMATION: Synthetic peptide sequence
<220> FEATURE:
<221> NAME/KEY: MISC_FEATURE
<222> LOCATION: (1)..(1)
<223> OTHER INFORMATION: Myristoylated
<220> FEATURE:
<221> NAME/KEY: MISC_FEATURE
<222> LOCATION: (6)..(6)
<223> OTHER INFORMATION: amide-terminated amino acid

<400> SEQUENCE: 19

Ala Lys Lys Leu Ala Lys
1               5

<210> SEQ ID NO 20
<211> LENGTH: 6
<212> TYPE: PRT
<213> ORGANISM: Artificial sequence
<220> FEATURE:
<223> OTHER INFORMATION: Synthetic peptide sequence
<220> FEATURE:
<221> NAME/KEY: MISC_FEATURE
<222> LOCATION: (1)..(1)
<223> OTHER INFORMATION: Myristoylated

<400> SEQUENCE: 20

Ala Lys Lys Ala Leu Lys
1               5

<210> SEQ ID NO 21
<211> LENGTH: 6
<212> TYPE: PRT
<213> ORGANISM: Artificial sequence
<220> FEATURE:
<223> OTHER INFORMATION: Synthetic peptide sequence
<220> FEATURE:
<221> NAME/KEY: MISC_FEATURE
<222> LOCATION: (1)..(1)
<223> OTHER INFORMATION: Myristoylated
<220> FEATURE:
<221> NAME/KEY: MISC_FEATURE
<222> LOCATION: (6)..(6)
```

```
<223> OTHER INFORMATION: amide-terminated amino acid

<400> SEQUENCE: 21

Ser Thr Lys Thr Thr Lys
1               5

<210> SEQ ID NO 22
<211> LENGTH: 8
<212> TYPE: PRT
<213> ORGANISM: Artificial sequence
<220> FEATURE:
<223> OTHER INFORMATION: Synthetic peptide sequence
<220> FEATURE:
<221> NAME/KEY: MISC_FEATURE
<222> LOCATION: (1)..(1)
<223> OTHER INFORMATION: Myristoylated
<220> FEATURE:
<221> NAME/KEY: MISC_FEATURE
<222> LOCATION: (8)..(8)
<223> OTHER INFORMATION: amide-terminated amino acid

<400> SEQUENCE: 22

Ser Arg Val Ser Arg Arg Ser Arg
1               5

<210> SEQ ID NO 23
<211> LENGTH: 9
<212> TYPE: PRT
<213> ORGANISM: Artificial sequence
<220> FEATURE:
<223> OTHER INFORMATION: Synthetic peptide sequence
<220> FEATURE:
<221> NAME/KEY: MISC_FEATURE
<222> LOCATION: (1)..(1)
<223> OTHER INFORMATION: Myristoylated
<220> FEATURE:
<221> NAME/KEY: MISC_FEATURE
<222> LOCATION: (9)..(9)
<223> OTHER INFORMATION: amide-terminated amino acid

<400> SEQUENCE: 23

Leu Ala Lys Leu Ala Lys Lys Ala Phe
1               5

<210> SEQ ID NO 24
<211> LENGTH: 9
<212> TYPE: PRT
<213> ORGANISM: Artificial sequence
<220> FEATURE:
<223> OTHER INFORMATION: Synthetic peptide sequence
<220> FEATURE:
<221> NAME/KEY: MISC_FEATURE
<222> LOCATION: (1)..(1)
<223> OTHER INFORMATION: Myristoylated

<400> SEQUENCE: 24

Leu Ala Lys Lys Ala Leu Lys Ala Phe
1               5

<210> SEQ ID NO 25
<211> LENGTH: 6
<212> TYPE: PRT
<213> ORGANISM: Artificial Sequence
<220> FEATURE:
<223> OTHER INFORMATION: Synthetic peptide sequence
<220> FEATURE:
<221> NAME/KEY: MISC_FEATURE
<222> LOCATION: (1)..(6)
<223> OTHER INFORMATION: All of these amino acids are "d" amino acids.
<220> FEATURE:
<221> NAME/KEY: MISC_FEATURE
<222> LOCATION: (1)..(1)
```

-continued

<223> OTHER INFORMATION: Myristoylated

<400> SEQUENCE: 25

Lys Leu Ala Lys Lys Leu
1               5

<210> SEQ ID NO 26
<211> LENGTH: 6
<212> TYPE: PRT
<213> ORGANISM: Artificial Sequence
<220> FEATURE:
<223> OTHER INFORMATION: Synthetic peptide sequence
<220> FEATURE:
<221> NAME/KEY: MISC_FEATURE
<222> LOCATION: (1)..(1)
<223> OTHER INFORMATION: Myristoylated
<220> FEATURE:
<221> NAME/KEY: MISC_FEATURE
<222> LOCATION: (6)..(6)
<223> OTHER INFORMATION: amide-terminated amino acid

<400> SEQUENCE: 26

Thr Lys Thr Ser Lys Ser
1               5

<210> SEQ ID NO 27
<211> LENGTH: 5
<212> TYPE: PRT
<213> ORGANISM: Artificial Sequence
<220> FEATURE:
<223> OTHER INFORMATION: Synthetic peptide sequence
<220> FEATURE:
<221> NAME/KEY: MISC_FEATURE
<222> LOCATION: (1)..(1)
<223> OTHER INFORMATION: Myristoylated
<220> FEATURE:
<221> NAME/KEY: MISC_FEATURE
<222> LOCATION: (5)..(5)
<223> OTHER INFORMATION: amide-terminated amino acid

<400> SEQUENCE: 27

Lys Arg Gly Asp Arg
1               5

<210> SEQ ID NO 28
<211> LENGTH: 5
<212> TYPE: PRT
<213> ORGANISM: Artificial Sequence
<220> FEATURE:
<223> OTHER INFORMATION: Synthetic peptide sequence
<220> FEATURE:
<221> NAME/KEY: MISC_FEATURE
<222> LOCATION: (1)..(1)
<223> OTHER INFORMATION: Myristoylated
<220> FEATURE:
<221> NAME/KEY: MISC_FEATURE
<222> LOCATION: (5)..(5)
<223> OTHER INFORMATION: amide-terminated amino acid

<400> SEQUENCE: 28

Lys Ser Ser Lys Ser
1               5

<210> SEQ ID NO 29
<211> LENGTH: 4
<212> TYPE: PRT
<213> ORGANISM: Artificial Sequence
<220> FEATURE:
<223> OTHER INFORMATION: Synthetic peptide sequence
<220> FEATURE:
<221> NAME/KEY: MISC_FEATURE
<222> LOCATION: (1)..(1)

```
<223> OTHER INFORMATION: Myristoylated
<220> FEATURE:
<221> NAME/KEY: MISC_FEATURE
<222> LOCATION: (4)..(4)
<223> OTHER INFORMATION: amide-terminated amino acid

<400> SEQUENCE: 29

Lys Thr Thr Lys
1

<210> SEQ ID NO 30
<211> LENGTH: 5
<212> TYPE: PRT
<213> ORGANISM: Artificial Sequence
<220> FEATURE:
<223> OTHER INFORMATION: Synthetic peptide sequence
<220> FEATURE:
<221> NAME/KEY: MISC_FEATURE
<222> LOCATION: (1)..(1)
<223> OTHER INFORMATION: Myristoylated
<220> FEATURE:
<221> NAME/KEY: MISC_FEATURE
<222> LOCATION: (5)..(5)
<223> OTHER INFORMATION: The amino acid at this location is a "d" amino
      acid.
<220> FEATURE:
<221> NAME/KEY: MISC_FEATURE
<222> LOCATION: (5)..(5)
<223> OTHER INFORMATION: amide-terminated amino acid

<400> SEQUENCE: 30

Lys Lys Ala Leu Lys
1               5

<210> SEQ ID NO 31
<211> LENGTH: 6
<212> TYPE: PRT
<213> ORGANISM: Artificial Sequence
<220> FEATURE:
<223> OTHER INFORMATION: Synthetic peptide sequence
<220> FEATURE:
<221> NAME/KEY: MISC_FEATURE
<222> LOCATION: (1)..(1)
<223> OTHER INFORMATION: Myristoylated

<400> SEQUENCE: 31

Leu Lys Lys Ala Leu Lys
1               5

<210> SEQ ID NO 32
<211> LENGTH: 4
<212> TYPE: PRT
<213> ORGANISM: Artificial Sequence
<220> FEATURE:
<223> OTHER INFORMATION: Synthetic peptide sequence
<220> FEATURE:
<221> NAME/KEY: MISC_FEATURE
<222> LOCATION: (1)..(1)
<223> OTHER INFORMATION: Myristoylated
<220> FEATURE:
<221> NAME/KEY: MISC_FEATURE
<222> LOCATION: (4)..(4)
<223> OTHER INFORMATION: amide-terminated amino acid

<400> SEQUENCE: 32

Lys Ala Lys Leu
1

<210> SEQ ID NO 33
<211> LENGTH: 4
<212> TYPE: PRT
<213> ORGANISM: Artificial Sequence
```

```
<220> FEATURE:
<223> OTHER INFORMATION: Synthetic peptide sequence
<220> FEATURE:
<221> NAME/KEY: MISC_FEATURE
<222> LOCATION: (1)..(1)
<223> OTHER INFORMATION: Myristoylated
<220> FEATURE:
<221> NAME/KEY: MISC_FEATURE
<222> LOCATION: (4)..(4)
<223> OTHER INFORMATION: amide-terminated amino acid

<400> SEQUENCE: 33

Leu Ala Lys Lys
1
```

POLYMERIC BIOSURFACTANTS

CROSS-REFERENCE TO RELATED APPLICATIONS

This application claims priority to U.S. Provisional Application Ser. No. 60/809,825 filed Jun. 1, 2006.

STATEMENT OF FEDERALLY SPONSORED RESEARCH

Not Applicable.

FIELD OF INVENTION

The present invention is directed to biosurfactants that can self-assemble or auto-aggregate into polymeric micellar structures and their use in topically-applied dermatologic products. The invention relates in particular to polymeric acylated biosurfactants having low critical micelle concentrations (from about 1.0 to about 200 ppm) in Minimal Essential Media that have the ability to increase metabolic soluble proteins. Additionally, they have comparatively low toxicity—preferably, an $LD_{50}$ of greater 200 ppm in 37 year-old female fibroblast cells—as well as the ability to increase synthesis of extracellular skin matrix proteins and/or increase rates of cell turnover.

BACKGROUND OF THE INVENTION

Surfactants as a class of molecules are well-known to formulators of topically-applied products. Biosurfactants are a specific group of surfactants derived from naturally-occurring raw materials which can be easily degraded by proteases. Like standard surfactants they have both a water-soluble and a water-insoluble group on the same molecule, generally defined as a "head and tail". As such, they have an affinity for both hydrophilic and lipophilic materials (e.g., oils, and more significantly for purposes of the present invention, cell membranes); thus, these are also described as amphipathic molecules. Biosurfactants of the present invention possess a high degree of affinity for cell membranes without the apparent disruption associated to standard surfactants at similar concentrations. They orientate themselves in a manner to lower surface tension between the incompatible "heads and tails". As the concentration of biosurfactant increases, the interfacial surface becomes saturated, until a minimum surface tension, the so-called the critical micelle concentration ("CMC"), is reached. If biosurfactant is added beyond the CMC, micelles or aggregates form. The CMC is generally expressed in millimoles (mM) and is dependent on the temperature and ionic strength of the media. These aggregates vary in particle size and shape. The polymeric biosurfactant aggregates within the scope of the present invention typically have particle sizes in the nano-range, from about 5 to 100 nanometers.

In skin care products, sodium dodecyl sulfate is a commonly-used anionic surfactant that acts as a wetting agent, emulsifier or cleansing agent. It has a CMC in distilled water of about 8.13 mM (or ~2400 ppm). Quaternary compounds are widely-used cationic surfactants. Dodecyl trimethyl ammonium bromide is representative of this class of compounds and has a CMC of about 14.6 mM (or ~4300 ppm) in distilled water. By way of comparison, the CMC of phospholipids—the principal components of the cell membranes (e.g., diacyl phosphatidyl cholines)—range from about $5 \times 10^{-3}$ mM to about $4.7 \times 10^{-7}$ mM (~3 ppm-~0.003 ppm). See, e.g., D. Datta, *Membrane Biochemistry* (1987). Polymeric biosurfactants of the present invention have a CMC between the representative anionic and cationic compounds as well as cells membrane phospholipids discussed above.

Conventional surfactants, however, are known to cause irritation, inflammation and other negative sequelae. This is due, in part, to defatting the skin, removing necessary oils as well as rapid penetration to the epidermal layer. Surprisingly and unexpectedly, the polymeric biosurfactants of the present invention do not have these drawbacks at similar concentrations.

As discussed below, the use of amino acid sequences in skin care products is known in the art. Some such sequences are commercially available as acylated moieties (e.g., acetyl, myristoyl, palmitoyl). In general, acylation is a well-known technique to those of skill in the art for enhancing penetration of a water-loving or hydrophilic ingredient into the skin. The surface of normal skin is highly hydrophobic preventing significant penetration by hydrophilic substances. However, the properties of an acylated amino acid sequence can vary greatly in terms of toxicity which, in turn, affects its ultimate usefulness. Surprisingly and unexpectedly, many of the polymeric acylated biosurfactants of the present invention have comparatively low toxicity to mammalian cells (on the order of $LD_{50} > 200$) while at the same time maintaining a relatively high degree of toxicity for prokaryotic life forms.

Moreover, unlike prior art acylated amino acid sequences, the polymeric biosurfactants of the present invention have the ability to increase the synthesis of skin matrix proteins (e.g., elastin, fibronectin, collagen) and/or increase cell turnover rates while not causing a concomitant increase in the synthesis of enzymes that degrade these proteins (e.g., matrix metalloproteinases). Additionally, surprisingly and significantly, biosurfactants of the present invention do not cause an increase in inflammatory proteins, notably interleukin 6 and interleukin 8. This combination of properties makes these compounds uniquely suited to skin care applications.

The ability of polymeric biosurfactants of the present invention to effectively wet surfaces at low CMCs confers another surprising and unexpected property—broad spectrum antimicrobial activity. Polymeric biosurfactants of the present invention have the ability to inhibit the growth or kill a variety of microorganisms, including *Escherichia coli* (*E. coli*), *Pseudomonas aeruginosa* (*P. aeruginosa*), *Staphylococcus aureus* (*S. aureus*) and *Candida albicans* (*C. albicans*).

In the fields of personal care and dermatology, there has been, and continues to be, a need for highly effective multifunctional ingredients. The use of ingredients of this type helps to mitigate problems common to topical skin care formulations—e.g., instability (due to incompatibility of ingredients) as well decreased efficacy of active ingredients over time (due to interactions among the ingredients). Multifunctional ingredients—particularly those with low propensity to cause irritation, inflammation or other negative sequelae—are in high demand not only among formulators but also among increasingly demanding and sophisticated consumers. Taken in combination, the favorable properties of the polymeric biosurfactants of the present invention make them multifunctional ingredients that surprisingly and unexpectedly meet the heretofore unmet need for products with comparatively low toxicity that both help to restore, maintain and improve dermatologic conditions associated with disease, aging and/or environmental stressors while, in many instances, at the same time inhibiting microbial growth.

Prior Art Amino Acid Sequences Used in Skin Care Products

The following cosmetic ingredients, each consisting of two amino acids, are commercially available: Dipeptide-1 (Tyrosine and Arginine residues); Dipeptide-2 (Valine and Tryptophan residues); Dipeptide-4 (Phenylalanine and Tryptophan residues). Unless otherwise indicated, cosmetic ingredients are described by their assigned name in the International Cosmetic Ingredient (INCI) Dictionary and Handbook (10$^{th}$ Edition) published by the Cosmetic Toiletry and Fragrance Association ("CTFA"). The INCI Dictionary does not specify amino acid sequences or the amounts of each amino acid residue. As discussed below, a tripeptide may be described in the INCI Dictionary as containing two amino acid residues without indicating whether one of the two listed amino acids is present twice or whether the third amino acid in the peptide sequence is selected from the group of eighteen other naturally-occurring amino acids.

US Patent Application Publication No. 2003/0166510 teaches the use of ionic metal-peptide complexes in an amount effective to remodel the skin and diminish or remove skin blemishes. (Granted U.S. patents and published U.S. patent applications referenced herein are, to the extent pertinent, incorporated by reference.) Skin blemishes taught in this reference include scars (e.g., from wounds, acne), skin tags, calluses, benign skin moles, stretch marks, facial keratoses, solar lentigines or vitiligo spots. According to this reference, ionic metals—copper(II), tin(II), tin(IV), and zinc (II) and salts thereof—are complexed with chemically-synthesized di-, tri- and tetrapeptides. Phe-Phe and Gly-Gly are specifically taught as dipeptide fragments that may be complexed with the above-listed ionic metals.

Spanish Patent Application Publication No. ES2020148 teaches a biosurfactant consisting of a fatty acid chain of 9-17 carbon atoms, saturated or unsaturated, attached to the N-terminus of Arginine in any of the L-, D-, or DL forms followed by a second amino acid selected from any of the twenty naturally-occurring amino acids. The specific amino acid sequences Arg-Gly, Arg-Ser and Arg-Phe are taught.

Tripeptide-1, a synthetic peptide containing three amino acid residues—Glycine, Histidine and Lysine—is commercially-available from Vincience under the tradename Kollaren C.P.P. and as Kollaren by I.E.B. The mixture of Tripeptide-1 with water, urea, glucose and Guanidine HCl is sold as Kollaren by Atrium Biotechnologies. The Gly-His-Lys sequence is described in the literature as a scavenger of reactive carbonyl species ("RCS") which are byproducts of cellular metabolic processes including lipid peroxidation and glycation. RCS have been associated with crosslinking of collagen and attendant loss of skin elasticity. See, Puig at al., "Peptides as Active Ingredients in Cosmetics," *Cosmetics and Toiletries Manufacture Worldwide*, pp. 121-125. This amino acid sequence does not have a CMC. Moreover, it does not form polymeric aggregates. Accordingly, it is not a biosurfactant within the scope of the present invention.

Acetyl Tripeptide-1 is the reaction product of acetic acid and is therefore not a biosurfactant within the scope of the present invention. As a general matter, acetylation does not confer sufficient amphipathic properties needed to function as biosurfactant.

Biotinyl tripeptide is formed by grafting vitamin H (biotin) on the tripeptide Gly-His-Lys. US Patent Application Publication No. 2006/0067905 describes a method for treating hair loss by administering oleanolic acid, apigenin and Biotinyl-Gly-His-Lys. The biotinyl moiety does not confer sufficient hydrophobicity to produce biosurfactant properties.

Palmitoyl Tripeptide-1, also described as Pal-GKH, is the reaction product of Tripeptide-1 and palmitic acid. It is available from Sederma under the tradename Lipo-GKH. When acid-terminated, this lipo-oligopeptide sequence has no measurable antimicrobial activity; moreover, it is toxic to mammalian cells at comparatively low concentrations (e.g., $LD_{50}$ of about 50 ppm). For these reasons, this lipo-oligopeptide is not within the scope of the present invention.

US Patent Application Publication No. 2004/0120918 at Paragraph #0008 describes Pal-Gly-His-Lys as Biopeptide CL available from Sederma. The INCI name for this tripeptide is Palmitoyl Oligopeptide which, according to the INCI Dictionary, is the palmitic acid ester of a synthetic peptide of two or more of the following amino acid residues: Alanine, Arginine, Aspartic Acid, Glycine, Histidine, Lysine, Proline, Serine or Valine.

Pal-Gly-His-Lys with the free acid or amide at the C-terminus exhibit significant toxicity in mammalian cell lines (i.e., having $LD_{50}$<100 in 37-year-old female fibroblast cells) and for this reason are not within the scope of the present invention.

US Patent Application Publication No. 2004/0132667 teaches a sequence of three amino acids—Glycine, Histidine and Lysine residues. A preferred tripeptide has the specific amino acid sequence Gly-His-Lys. Analogs of this sequence are taught to include those in which one or more of the three amino acids are reorganized or rearranged within the sequence (e.g., Gly-Lys-His). This publication also teaches substitution of up to two of the three amino acids. Amino acids that may be substituted for Gly are taught to have an aliphatic side chain such as, without limitation, beta-Ala, Ala, Val, Leu, Pro and Ile. Of these, Ala, Leu and Ile are preferred. Amino acids that are taught to be substituted for Lys or His include those having a side chain that includes, predominantly, a charged nitrogen at a pH of about 6 (e.g., Pro, Lys, Arg, His, Desmosine and Isodesmosine). Most preferably, Lys is replaced with Ornithine, Arginine, or Citrulline.

The '667 application further teaches attaching to the above-described substituted or rearranged amino acid sequences acyl-moieties derived from: acetic acid, capric acid, lauric acid, myristic acid, octanoic acid, palmitic acid, stearic acid, behenic acid, linoleic acid, linolenic acid, lipoic acid, oleic acid, isostearic acid, elaidoic acid, 2-ethylhexaneic acid, coconut oil fatty acid, tallow fatty acid, hardened tallow fatty acid, palm kernel oil fatty acid, lanolin fatty acid. These derivatives are further taught to be straight-chain or branched-chain, long or short chain, saturated or unsaturated, substituted with a hydroxy, amino, acyl amino, sulfate or sulfide groups, or unsubstituted. Preferred acyl groups are taught to include palmitoyl and myristoyl. By teaching replacement of Lysine with Alanine or Arginine, and acylating the resulting three amino acid sequence with a palmitoyl or myristoyl group, the '667 Publication teaches the following acylated peptides: Pal-Gly-His-Arg; Pal-Arg-His-Ala; Pal-Arg-His-Gly; Pal-Ala-His-Arg; Myr-Gly-His-Arg; Myr-Arg-His-Ala; Myr-Arg-His-Gly; Myr-Ala-His-Arg. This patent publication does not, however, teach C-terminus amidation for these acylated tripeptides or the antimicrobial, stimulatory and/or proliferative properties of the polymeric biosurfactants of the present invention. Moreover, the tripeptides disclosed in this publication have only one positively-charged amino acid residue at neutral pH. As discussed below, the polymeric biosurfactants of the present invention largely contain two, and often, three positively-charged amino acid residues.

Tripeptide-2 is a synthetic peptide available under the tradename I.E.L. from Vincience. According to the INCI Dictionary, it contains two amino acid residues—Tyrosine and Valine. This amino acid sequence does not have a CMC and is therefore not a biosurfactant within the scope of the present invention.

Tripeptide-3, having the amino acid sequence Gly-His-Arg, has been disclosed in marketing materials by Therapeutic Peptides Inc. This amino acid sequence does not have a CMC and is therefore not a biosurfactant within the scope of the present invention.

The scientific literature reports that Gly-His-Lys-Cu, a copper tripeptide, has a stimulatory effect on collagen synthesis by fibroblasts. See Maquart F X at al., *FEBS Lett.* 238(2):343-6 (1988). See also, Oddos T et al. "Requirement of Copper and Tripeptide Glycyl-L-Histidyl-L-Lysine-Cu (GHK) Complex Formation for Collagen Synthesis Activity in Normal Human Dermal Fibroblasts" presented at the 60th Annual Meeting American Academy of Dermatology (New Orleans, La., February 2002). Additionally, this copper tripeptide has been reported to promote wound healing. See, Fish, et al., *Wounds* 3:171 (1991); Mulder et al., *Wound Rep. and Regen.* 2: 259 (1994).

Cosmetic use of Gly-His-Lys-Cu is described in U.S. Pat. Nos. 5,135,913 and 5,348,943 both assigned to ProCyte Corporation. Commercially, this copper tripeptide is used as an ingredient in Neutrogena Visibly Firm Night Cream as well as in products offered by ProCyte Corp. under the brand names Simple Solutions® Anti-Aging Skin Care (sold through spas and aestheticians) and Neova® (sold through dermatologists).

German Patent Application DE 41 27 790 A1, published on Feb. 25, 1993, teaches the use of Mg, Mn, Zn and Ge complexes of Gly-His-Lys to improve the condition of the skin. The Bibliographic Data for this patent application, as published on the European Patent Office website espacenet.net, also teaches tripeptides where each of the three constituent amino acids of the peptide is one of Lysine, Hydroxylysine, Proline, Hydroxyproline, Arginine, Glycine or Histidine. More particularly, a tripeptide conforming to the formula B1-B2-B3 is taught, where each of B1, B2 and B3 are one of the seven above-listed amino acids.

German Patent Application DE 42 44 418 A1 teaches cosmetic and pharmaceutical compositions containing Gly-His-Lys and Gly-Asp-Ser, both as tripeptides as well as part of a longer peptide moiety at concentrations of 1 picoM to 0.01M. These compositions are taught to be prepared either by mild hydrolysis of collagen, elastin, keratin or connective tissue with hydrochloric acid or partial hydrolysis using *C. histolyticum* collagenase. Among the disclosed anti-aging skin care applications are stimulation of collagen synthesis and scavenging of free radicals.

French Patent Application FR 2 826 577 A1 teaches peptides containing the sequence Lys-Pro-Val. According to this application, topical application of compositions containing this sequence increases the expression of genes coding for enzymes involved in the synthesis of epidermal lipids (i.e., cholesterol, fatty acids, and sphingolipids), thereby improving skin barrier function. The disclosed peptide sequence has no CMC and is therefore not a biosurfactant within the scope of the present invention.

U.S. Pat. No. 5,493,894 teaches compositions for treating skin wrinkles containing tri-, tetra- and pentapeptide moieties composed of at least three Arginine or Lysine residues. Among the specifically disclosed tripeptides are: (i) H-Arg-Lys-Arg-OH; (ii) $H_3C$—C(O)-Arg-Lys-Arg-$NH_2$. These two specifically-disclosed sequences do not have CMCs and therefore are not biosurfactants within the scope of the present invention.

US Patent Application Publication No. 2003/0166510 teaches the use of ionic metal-tripeptide complexes in which one of copper(II), tin(II), tin(IV), or zinc(II) is complexed with the following amino acid sequences: Gly-His-Lys; Gly-Gly-His; His-Gly-Gly; Gly-Gly-Gly; Ala-Gly-His; Gly-Cys-Gly; His-Gly-His. The above described metal-tripeptide complexes do not have CMCs and therefore are not biosurfactants within the scope of the present invention.

US Patent Application Publication 2006/0013794 teaches cosmetic, dermatological and/or pharmaceutical compositions comprising tri-, tetra-, penta-, hexa-, hepta- and nonpeptides containing the amino acid sequence Arg-Gly-Ser.

Tetrapeptide-1 is the INCI name assigned to a synthetic peptide containing four amino acid residues—Leucine, Proline, Threonine and Valine. It is sold under the tradename I.E.L. Leuococytar Elastase Inhibitor by Vincience. As discussed above, amino acid sequences alone do not have sufficient hydrophobicity to self-aggregate and, therefore do not have a CMC and are not biosurfactants within the scope of this patent. Moreover, none of the four amino acids in this compound have a charge. For this additional reason, this compound is not within the scope of the present invention.

Tetrapeptide-4 is the INCI name assigned to a synthetic tetrapeptide sold under the tradename Collasyn 4 GG by Therapeutic Peptides Inc. It contains three amino acid residues—Glycine, Glutamic Acid and Proline. More particularly, this peptide has the sequence Gly-Glu-Pro-Gly. For the reasons discussed above, this amino acid sequence is not a biosurfactant (i.e., no CMC, no self-aggregation) within the scope of the present invention.

Therapeutic Peptides Inc. has also disclosed the acylated amino acid sequence Myr-Gly-Glu-Pro-Gly under the tradename Collasyn 414 GG. At concentrations of 500 ppm or less, this sequence does not inhibit the growth of *E. coli, P. acnes, P. aeruginosa, S. aureus* and/or *C. albicans* and accordingly is not within the scope of the present invention.

Acetyl Tetrapeptide-1 is the reaction product of acetic acid and a synthetic peptide containing three amino acid residues—Glycine, Histidine and Lysine. It is sold under the tradename Kollaren 6 by I.E.B. For the reasons discussed above, this amino acid sequence is not a biosurfactant (i.e., no CMC, no self-aggregation) within the scope of the present invention.

Acetyl Tetrapeptide-2 is the reaction product of acetic acid and a synthetic peptide containing four amino acid residues—Aspartic Acid, Lysine, Tyrosine and Valine. Manufactured by I.E.B., the product is sold under the tradename Thymulen 4 by Atrium Biotechnologies. Product literature describes Thymulen 4 as a biomimetic peptide derived from thymopoietin having skin regenerative properties. For the reasons discussed above, this amino acid sequence is not a biosurfactant (i.e., no CMC, no self-aggregation) within the scope of the present invention.

Rigin, a tetrapeptide having the sequence Gly-Gln-Pro-Arg, is reported in the scientific literature by Veretennikova, et al., *Int. J. Peptide Protein Res.*, 17:430 (1981). Palmitoyl Tetrapeptide is described in the INCI Dictionary as the reaction production of palmitic acid and a synthetic peptide containing Glycine, Glutamine, Proline and Arginine. It is commercially-available from Sederma.

At concentrations of 500 ppm or less, the acylated amino acid sequence Pal-Gly-Gln-Pro-Arg-acid does not inhibit the growth of microorganisms including *E. coli* and *P. aeruginosa*, and accordingly is not within the scope of the present invention. Moreover, both this compound and its amide-terminated analog exhibit significant toxicity in mammalian cell lines (i.e., having $LD_{50}$<100 in 37 year-old female fibroblast cells).

Eyeliss is the tradename of a raw material concentrate combining two peptides and is marketed by Sederma for helping to reduce the appearance of puffiness and dark circles under the eyes. As described in International Patent Application PCT FR-03/00441, it is a combination of hesperidin methyl chalcone and two acylated peptide fragments—Valyl-Tryptophane and N-Palmitoyl-Gly-Gln-Pro-Arg. More generally, this PCT Application describes tri-, tetra- and pentapeptides beginning with a $C_2$-$C_{22}$ carbon chain and terminating in the sequence Pro-Arg-OH. According to U.S. Pat. No. 6,974,799, the Val-Trp dipeptide has no significant collagen stimulating activity and its combination with the Gly-Gln-Pro-Arg tetrapeptide does not exhibit any enhancement in this property over the levels realized by the use of the tetrapeptide alone.

Matrixyl 3000 is the tradename for a combination of two acylated peptides, N-Palmitoyl-Gly-Gln-Pro-Arg and N-Palmitoyl-Gly-His-Lys. U.S. Pat. No. 6,974,799 teaches topical compositions comprising (i) between about 0.00001% and about 0.5% (based on the total weight of the composition) of at least one "rigin-based tetrapeptide" (defined as Gly-Gln-Pro-Arg) and between about 0.00001% and about 1.0% of at least one tripeptide Gly-His-Lys, where the tripeptide is present in an amount greater than the tetrapeptide and (ii) at least one additional skin care ingredient. The disclosed composition is taught to be useful in reducing visible signs of aging and stretch marks as well as visible dark circles under the eyes.

DE 41 27 790 teaches the following tetrapeptides as part of an oligopeptide metal complex with Mg, Mn, Cu, Zn, Ge, Ni, Fe, Mo and Co: (i) Gly-His-Lys-Lys; (ii) Gly-His-Lys-Gly; (iii) Gly-His-His-Gly; (iv) Gly-His-His-Lys; (v) Gly-His-Arg-Lys; (vi) Gly-His-Arg-Gly; (vii) Gly-His-pro-Lys; Gly-His-Pro-Lys; (ix) Hyp-Gly-Lys-Lys; (x) Hyp-Gly-His-Lys; (xi) Hyp-Gly-Arg-Lys; (xii) Hyp-Gly-Pro-Lys; (xiii) Arg-Gly-Lys-Lys; (xiv) Arg-Gly-Lys-Lys; (xv) Arg-Gly-His-Lys; (xvi) Arg-Gly-His-Lys; (xvii) Arg-Gly-Arg-Lys; (xviii) Arg-Gly-Arg-Lys; (xix) Arg-Gly-Pro-Lys; and (xx) Arg-Gly-Arg-Lys, where Hyp is hydroxyproline.

The Bibliographic Data for German Patent Application DE 41 27 790, as published on ep.espacenet.com, also teaches tetrapeptides where each of the first three amino acids of the peptide is one of Lysine, Hydroxylysine, Proline, Hydroxyproline, Arginine, Glycine or Histidine and the fourth amino acid is the same as one of the preceding three amino acids. More particularly, tetrapeptides conforming to the formulae B1-B2-B3-B1, B1-B2-B3-B2 and B1-B2-B3-B3. The oligopeptide metal complexes as disclosed in this application do not have a CMC and do not self-aggregate. For these reasons they are not biosurfactants within the scope of the present invention.

U.S. Pat. No. 5,493,894 specifically teaches compositions for treating skin wrinkles containing the following tetrapeptides: (i) H-Arg-Gly-Arg-Lys-OH and (ii) H-Lys-Arg-Ser-Arg-NH$_2$. These are not biosurfactants and thus are not within the scope of the present invention.

US Patent Application Publication No. 2003/0166510 teaches ionic metals complexed with the tetrapeptide Gly-His-Lys-His. Topical compositions comprising this metal ion/tetrapeptide complex are taught to be useful in diminishing or removing skin blemishes.

Therapeutic Peptides Inc. has disclosed in trade literature the amide-terminated VPAA tetrapeptide sequence as well as Myristoyl Tetrapeptide-5, an acylated synthetic peptide having the VPAA sequence. The latter is commercially available under the tradename Collasyn 414 VA. At concentrations of 500 ppm or less, this acylated amino acid sequence does not inhibit the growth of microorganisms, including *E. coli*. Moreover, this sequence contains no charged amino acid residues. Accordingly, for these reasons, Myr-Val-Pro-Ala-Ala is not within the scope of the present invention.

U.S. Pat. No. 4,665,053 teaches "bifunctional" synthetic lipopeptides, which are further defined as functioning both as inhibitors of elastolytic activity and protectors of elastic fibers. Additionally, these lipopeptide moieties are described as being capable not only of recognizing and becoming fixed on elastic fiber but also of recognizing and neutralizing the active site of elastases. More particularly, this reference teaches lipopeptides having in two sequential L-Alanine residues conforming to the formula: R—X—$(P_1)_x$-(L-Ala-L-Ala-$P_2$)-A where $P_1$ is an amino acid sequence, two to eight residues in length; x is 0 or 1; R is an acylated hydrophobic carboxylic acid. $P_2$ is taught to be one of L-Ala, L-Val, L-Pro-L-Ala or L-Pro-L-Val. A is the C-terminus in the form of acid, aldehyde, alcohol, amide or chloromethyl ketone.

Palmitoyl Pentapeptide-2 is the reaction of palmitic acid and a synthetic peptide consisting of four amino acid residues—Tyrosine, Glycine, Phenylalanine and Leucine. It is available from Sederma. This acylated amino acid sequence contains no charged residues and accordingly is not within the scope of the present invention.

Pentapeptide-3 is sold under the tradename Matrixyl by Sederma. It described in the INCI Dictionary as the reaction product of palmitic acid and a synthetic peptide consisting of Lysine, Threonine and Serine residues. The INCI Dictionary does not list the amino acid sequence of this material. Without further information, and interpreting "consisting" to mean that only the three listed amino acid residues are present in the product, this reference would teach sixty combinations without suggesting which one(s) would have particular properties.

As disclosed in trade literature and marketing materials of finished goods companies, the amino acid sequence of the Matrixyl pentapeptide is Lys-Thr-Thr-Lys-Ser. This compound is further described in U.S. Pat. No. 6,620,419 which claims peptides according to the formula: $R_1$—X-Thr-Thr-Lys-$(AA)_n$-Y. X is defined as one of seven amino acids, with D or L orientation. Among the seven amino acids taught at the X position is Lysine. $R_1$ is taught to be hydrogen or a fatty acid chain of 2 to 22 carbons, which includes palmitoyl. $(AA)_n$ is taught to represent a chain of n amino acids where n varies from 0 to 5. Y is defined as $OR_2$ or $NR_2R_3$, where $R_2R_2$ may be hydrogen, resulting in acid and amide C-termini.

Pal-KTTKS-acid does not exhibit antimicrobial activity at a concentration of less than 500 ppm and therefore is not a polymeric biosurfactant within the scope of the present invention.

Collasyn 514KS is the tradename for Myristoyl Pentapeptide-3. This synthetic peptide contained Threonine, Serine and Lysine residues in the sequence Myr-KTTKS-amide and was available from Therapeutic Peptides Inc. This moiety does not result in an increase in soluble metabolic proteins, does not increase cell turnover, nor does it possess desired antimicrobial properties. For these reasons, Collasyn 514KS is not within the scope of the present invention.

DE 41 27 790 A1 teaches pentapeptides of the following sequences as being complexed with Mg, Mn, Cu, Zn, Ge, Ni, Fe, Mo and Co: (i) Hyp-Gly-Lys-Hyp-Gly; (ii) Hyp-Gly-His-Lys-Gly; (iii) Gly-Pro-Lys-Gly-Pro. These peptides are not acylated and therefore are not biosurfactants within the scope of the present invention.

The Bibliographic Data for German Patent Application DE 41 27 790, as published on ep.espacenet.com, also teaches pentapeptides where (i) each of the first three amino acids is one of Lysine, Hydroxylysine, Proline, Hydroxyproline, Arginine, Glycine or Histidine and (ii) the fourth and fifth amino acids are the same as one of the preceding three amino acids. More particularly, the bibliographic data teaches pentapeptides corresponding to the following six formulae: (i) B1-B2-B3-B1-B2; (ii) B1-B2-B3-B2-B3; (iii) B1-B2-B3-B2-B3; (iii) B1-B2-B3-B2-B1-B3; (iv) B1-B2-B3-B2-B1; (v) B1-B2-B3-B3-B2; and (vi) B1-B2-B3-B3-B1, where each of B1, B2 and B3 is Lysine, Hydroxylysine, Proline, Hydroxyproline, Arginine, Glycine or Histidine. These peptides are not acylated and therefore are not biosurfactants within the scope of the present invention.

Acetyl Pentapeptide-1 is sold under the tradename Thymulen by Atrium Biotechnologies. It is the reaction product of acetic acid and Pentapeptide-1. In product literature, Thymulen is described as inducing the secretion granulocyte-macrophage colony stimulating factor, resulting in a multiplication and a differentiation of keratinocytes. This peptide moiety does not have a measurable CMC and is therefore not a biosurfactant within the scope of the present invention.

Therapeutic Peptides Inc. has also offered for sale the following amide-terminated amino acid sequences: EVEDQ; DSDPR; GRKGD; GEESN; KKALK; KRGDR; LPPSR. Because these peptide moieties are not acylated they do not have a CMC and are not biosurfactants within the scope of the present invention.

U.S. Pat. No. 6,492,326 claims pentapeptides and/or pentapeptide derivatives and mixtures thereof in combination with an "additional skin care active" in a dermatologically-acceptable carrier. These additional skin care actives are taught to include di-, tri-, and tetrapeptides (and their derivatives) as well as retinoids, hydroxy-acids, anti-inflammatory, anti-fungal and anti-microbial agents.

WO97/18235 entitled "Peptide Conjugates, Use Thereof as a Drug and Compositions Containing Same" published in May 1997. Pentapeptides and pentapeptide derivatives are disclosed at page 6 #s 2, 5, 7, 9, 11 and at page 7 #14. Additional skin care actives, specifically antifungal and antimicrobial agents are taught in combination with the disclosed peptides at page 8, lines 19-24. WO97/18235 also teaches that the disclosed peptides and their derivatives can be used in creams, gels, milks, lotions, and sprays with excipients well-known in the cosmetics industry. Page 3 of this application further teaches that the peptide sequences can be acylated with straight-chain or branched, saturated or unsaturated, $C_1$-$C_{20}$ monocarboxylic acids. More particularly, this application discloses lipo-oligopeptides having the specific amino acid sequence Gly-His-Lys within the oligopeptide. The biosurfactants of the present invention do not contain this specific sequence.

Hexapeptides of the following amino acid sequences are taught by DE 41 27 790 A1 as being complexed with one of Mg, Mn, Cu, Zn, Ge, Ni, Fe, Mo and Co: (i) Gly-Pro-Arg-Gly-Pro-Hyp; (ii) Gly-His-Hyp-Gly-Lys-Pro; (iii) Gly-Lys-Pro-Gly-Arg-Hyp; (iv) Gly-Pro-Hyp-Gly-Pro-Pro; (v) Gly-His-Arg-Gly-His-Lys. Because these peptide moieties are not acylated they do not have a CMC and are not biosurfactants within the scope of the present invention.

Hexapeptide-1 is a synthetic peptide consisting of six amino acid residues—Alanine, Arginine, Histidine, Leucine, Phenylalanine and Tryptophan. Because these peptide moieties are not acylated they do not have a CMC and are not biosurfactants within the scope of the present invention.

Acetyl Hexapeptide-1, the reaction product of acetic acid and Hexapeptide-1, is sold under the tradename Melitane by Vincience. This peptide moiety does not have a measurable CMC and is therefore not a biosurfactant within the scope of the present invention.

Melitane 5 PP is the tradename for dextran and Acetyl Hexapeptide-1. Melitane 5 PS is the tradename for water dextran and Acetyl Hexapeptide-1. The PP and PS designators indicate, respectively, peptide powder and peptide solution. The PS product is described in trade literature as a peptide that mimics the activity of alpha melanocyte stimulating hormone, stimulating melanogenesis. Both are commercially available from I.E.B. This peptide moiety does not have a measurable CMC and is therefore not a biosurfactant within the scope of the present invention.

Acetyl Hexapeptide-3 is a synthetic peptide consisting of three amino acids—Arginine, Methionine and acetylated Glutamic Acid. It is sold under the tradename Argireline by Lipotec. This peptide moiety does not have a measurable CMC and is therefore not a biosurfactant within the scope of the present invention.

Hexapeptide-4 is a synthetic peptide containing Lysine, Threonine and Serine residues and is commercially available from Therapeutic Peptides Inc. under the tradename Collasyn 6KS. This peptide moiety is not acylated and does not have a CMC; accordingly, it is not a biosurfactant within the scope of the present invention.

Hexapeptide-5 is a synthetic peptide containing Valine, Tyrosine, Glutamic Acid, Proline and Isoleucine residues. It is commercially available from Therapeutic Peptides Inc. under the tradename Collasyn 6VY. This peptide moiety is not acylated and does not have a CMC; accordingly, it is not a biosurfactant within the scope of the present invention.

Hexapeptide-6 is a synthetic peptide having the sequence VEPIPY. It is commercially-available from Therapeutic Peptides, Inc. This peptide moiety is not acylated and does not have a CMC; accordingly, it is not a biosurfactant within the scope of the present invention.

The scientific literature describes the chemotactic activity of several components of the extracellular matrix including collagen, fibronectin, elastin and tropoelastin, the soluble precursor of elastin. The chemotactic activity of elastin for fibroblasts has reported to be associated with the repeating hexapeptide sequence Val-Gly-Val-Ala-Pro-Gly. See Senior R M et al., *J. Cell Biol.* 99(3): 870-874 (1984). As a sequence, Val-Gly-Val-Ala-Pro-Gly has also been reported to stimulate the growth of human skin fibroblasts. See, Kamoun A. et al., *Cell Adhes. Commun.*, 3(4): pp. 273-81 (1995). Because this peptide sequence is not acylated it does not have a CMC and is not a biosurfactant within the scope of the present invention.

Palmitoyl-Val-Gly-Val-Ala-Pro-Gly is an acylated hexapeptide available from Sederma under the tradename Biopeptide EL. The INCI name for Biopeptide EL is Palmitoyl Oligopeptide. Because this peptide sequence does not contain at least one charged amino acid moiety it is not within the scope of the present invention.

US Patent Application Publication No. 2004/0120918 teaches the use of a ceramide to improve the anti-aging activity of a polypeptide (or an acylated polypeptide) having an amino acid sequence of from 3 to 12 amino acids in length. The '918 Publication teaches N-acyl derivatives of the Val-Gly-Val-Ala-Pro-Gly hexapeptide, where the acyl chain is an alkoyl of 2-22 carbons, linear or branched, saturated or unsaturated, hydroxylated or non-hydroxylated. This publication more specifically teaches Biopeptide EL in combination with three ceramides, n-stearoyl-dihydrosphingosine, trihydroxypalmitamidohydroxy-propylmyristyl ether or palmitamidomyristylserinate. This specific hexapeptide amino acid sequence is not contained within the polymeric biosurfactants of the present invention.

The commercial product Bio-Bustyl, available from Sederma is a combination of Pal-VGVAPG and Pal-GHK. The INCI name for this compound is Glyceryl Polymethacrylate-Rahnella/Soy Protein Ferment-Water (Aqua)-Propylene Glycol-Glycerin-PEG-8-Palmitoyl Oligopeptide. Pal-VGVAPG does not contain a charged amino acid residue and is therefore not a polymeric biosurfactant within the scope of the present invention.

Myristoyl Hexapeptide-6 is available from Therapeutic Peptides Inc. under the tradename Collasyn 614VG. According to the INCI Dictionary, it is the reaction product of Myristic Acid with a synthetic peptide containing Valine, Glycine, Alanine and Proline residues. Collasyn 614VG does not contain a charged amino acid residue and is therefore not a polymeric biosurfactant within the scope of the present invention.

Acetyl Hexapeptide-7 is described in the INCI Dictionary as the reaction product of acetic acid and Hexapeptide-7. It is sold under the tradename Melitane 5 by Atrium Biotechnologies. Melitane 5 PP and 5 PS are mixtures of dextran and Acetyl-Hexapeptide-7, with 5 PS also containing water. Both are available from I.E.B. This peptide moiety does not have a measurable CMC and is therefore not a biosurfactant within the scope of the present invention.

Palmitoyl Oligopeptide is also the INCI designation for Biopeptide EN from Sederma. As further described in US Patent Application Publication No. 2002/0025303, Biopeptide FN is composed of Arginine, Aspartic Acid, Glycine, and Serine. None of the compositions of the present invention are composed of all four of these amino acids.

Hexapeptide-8 has been sold by Therapeutic Peptides Inc. as the amide-terminated sequence Ser-Thr-Lys-Thr-Thr-Lys. Because this peptide moiety is not acylated it does not have a CMC and is not a biosurfactant within the scope of the present invention.

WO 9962482 describes alkyl-heptapeptides where a 9- to 13-membered carbon chain is bound to the N-terminus of the heptapeptide sequence Glu-Leu-Leu-Val-Asp-Leu-X1, where X1 is an amino acid selected from the group consisting of the twenty naturally-occurring amino acids, hydroxyproline and homoserine. None of the compositions of the present invention contain the six amino acid sequence Glu-Leu-Leu-Val-Asp-Leu.

Nonapeptide-1 in a mixture with water and dextran is sold under the Melanostatine 5 by Atrium Biotechnologies. According to its product literature, it is a biomimetic peptide for skin whitening. Because this peptide moiety is not acylated it does not have a CMC and is not a biosurfactant within the scope of the present invention.

Therapeutic Peptides Inc. has offered for sale an amide-terminated nonapeptide having the sequence VQGEESNDK. Because this peptide moiety is not acylated it does not have a CMC and is not a biosurfactant within the scope of the present invention.

US Patent Application Publication 2005/0124545 teaches cosmetic, dermatological and/or pharmaceutical compositions containing fifteen amino acid sequence $X_1$-Y-Phe-Thr-$X_2$-Ala-Thr-Z-Ile-$X_3$-Leu-$X_4$-Phe-Leu-$X_5$. Each of $X_1$, $X_2$, $X_3$, $X_4$ and $X_5$ is defined as one of Arg, Lys or His. Y is defined as either Asp or Glu. Z is defined as either Asn or Gln. These specific amino acid sequences are not contained within the polymeric biosurfactants of the present invention. Moreover, because the peptide moieties according to the above formula are not acylated they do not have a CMC and are not biosurfactants within the scope of the present invention.

U.S. Pat. No. 5,492,894 to Bascom et al. teaches peptides having three to six amino acid residues, two of which are Arg and one of which is Lys, useful in the cosmetic treatment of mammalian skin wrinkles. The following thirty-eight amino acid sequences are disclosed: (1) RGRK; (2) KRSR; (3) RSRK; (4) YRSRKY; (5) YRSRK; (6) RSRKY; (7) TYRSRKYS; (8) SYRSRKYT; (9) SYRSRKYS; (10) TYRSRKYT; (11) RSRKYT; (12) TYRSRK; (13) RSRKYS; (14) SYRSRK; (15) YRSRKYT; (16) TYRSRKY; (17) YRSRKYS; (18) SYRSRKY; (19) NTYRSRKYSS; (20) NSYRSRKYTS; (21) NSYRSRKYSS; (22) NTYRSRKYTS; (23) RSRKYTS; (24) NTYRSRK; (25) RSRKYSS; (26) NSYRSRK; (27) YRSRKYTS; (28) NTYRSRKY; (29) YRSRKYSS; (30) NSYRSRKY; (31) TYRSRKYSS; (32) NTYRSRKYS; (33) SYRSRKYTS; (34) NSYRSRKYT; (35) SYRSRKYSS; (36) NSYRSRKYS; (37) TYRSRKYTS; and (38) NTYRSRKYT. Alkyloyl is among the groups that may be attached to the first amino acid in the sequence.

U.S. Pat. No. 6,875,744 teaches non-acylated peptides sequences, five to twenty-two amino acids in length comprising at least 80% Phenylalanine, Leucine, Alanine, and Lysine residues. The peptides disclosed in the '744 patent do not have CMCs and are not biosurfactants within the scope of the present invention.

SUMMARY OF THE INVENTION

The present invention is directed to polymeric acylated biosurfactants ("PABs") set out in the sequence listing in the table immediately following this paragraph having a critical micelle concentration of less than about 200 ppm in an aqueous environment of Minimal Essential Media ("MEM") Solution (as defined below) that reduce the surface tension in the aqueous environment to less than about 50 dynes/cm². More particularly, the PABs consist essentially of (i) an 8- to 22-membered carbon chain, branched or unbranched, saturated or unsaturated; (ii) four to nine amino acid residues, at least one, preferably at least two of which is/are charged; and (iii) an acid C-terminus or an amide C-terminus. As used in the present application, by charged amino acid is meant lysine, arginine, aspartic acid and glutamic acid. Surprisingly, PABs of the present invention have been found to have an ability to increase metabolic soluble proteins by at least about 20%. Additionally, they have comparatively low toxicity for mammalian cells—preferably, an $LD_{50}$ of greater 200 ppm in 37 year-old female fibroblast cells—as well as the ability to increase synthesis and/or slow degradation of extracellular skin matrix proteins.

The following sequence listing forms part of the specification and is included to further illustrate certain aspects of the present invention. The invention may be better understood by reference to one or more of these sequences in combination with the detailed description of the invention presented below.

| SEQ ID NO | Sequence |
| --- | --- |
| 1 | Myr-KAKA amide |
| 2 | Myr-AKAK amide |
| 3 | Pal-GRKG amide |

-continued

| SEQ ID NO | Sequence |
|---|---|
| 4 | Myr-GRKG amide |
| 5 | Myr-LAKK amide |
| 6 | Pal-GQPR amide |
| 7 | Myr-KLAKK amide |
| 8 | Pal-KLAKK acid |
| 9 | Myr-KKGEM amide |
| 10 | Myr-KRGKP amide |
| 11 | Pal-KRGDR acid |
| 12 | Myr-KKALK amide |
| 13 | Pal-KKALK amide |
| 14 | Pal-KKALK acid |
| 15 | Myr-KKLAK amide |
| 16 | Pal-GRKGD acid |
| 17 | Myr-GRKGD amide |
| 18 | Myr-KLAKKL acid |
| 19 | Myr-AKKLAK amide |
| 20 | Myr-AKKALK acid |
| 21 | Myr-STKTTK amide |
| 22 | Myr-SRVSRRSR amide |
| 23 | Myr-LAKLAKKAF amide |
| 24 | Myr-LAKKALKAF acid |
| 25 | Myr-d-[KLAKKL] acid |
| 26 | Myr-TKTSKS amide |
| 27 | Myr-KRGDR amide |
| 28 | Myr-KSSKS amide |
| 29 | Myr-KTTK amide |
| 30 | Myr-KKAL-d-[K]-amide |
| 31 | Myr-LKKALK acid |
| 32 | Myr-KAKL amide |
| 33 | Myr-LAKK amide |

The sequence listings in the above table are presented in the Sequence Listing at the end of this application and are recorded in computer readable form on the Compact Disc Sequence Listing that is submitted herewith for search purposes. The information in the written Sequence Listing is identical to the Compact Disc Sequence Listing. Unless otherwise noted (i.e., SEQ ID NO: 25 and SEQ ID NO: 30), amino acids in the PABs are in L form.

DETAILED DESCRIPTION OF THE INVENTION

The present invention is directed to polymeric acylated biosurfactants ("PABs") having a critical micelle concentration of less than about 200 ppm in an aqueous environment of MEM Solution that reduce the surface tension of the MEM Solution to less than about 50 dynes/cm$^2$ where the PABs consist essentially of (i) an 8- to 22-membered carbon chain, branched or unbranched, saturated or unsaturated; (ii) four to nine amino acid residues, at least one of which is charged; and (iii) an acid C-terminus or an amide C-terminus.

As used in the present application, "MEM Solution" is a 1,000 ml solution prepared by adding 10 grams of MEM Powder (as defined below) to 950 ml of deionized, distilled water at room temperature and mixing with gentle stirring. To this mixture is added 2.2 g of $NaHCO_3$ and 10 ml of Penicillin-Streptomycin Solution (as defined below). Deionized, distilled water is then added in a quantity sufficient to reach a final volume of 1,000 ml. The final pH of the MEM Solution is adjusted to 7.4-7.6 by slowly adding, with stirring, either 1 N NaOH or 1 N HCl. The MEM Solution is processed by membrane filtration through 0.2 μm filter using a positive pressure system. "MEM Powder", available from Invitrogen, Inc. (Carlsbad, Calif.) under the tradename GIBCO 41500, contains the following ingredients at the listed concentrations:

| Ingredient | Concentration (mg/L) |
|---|---|
| Calcium Chloride (anhyd.) | 200.00 |
| Potassium Chloride | 40.00 |
| Magnesium Sulfate (anhyd.) | 97.67 |
| Sodium Chloride | 6800.00 |
| Sodium Phosphate - $H_2O$ | 140.00 |
| D-Glucose | 1000.00 |
| Phenol Red | 10.00 |
| L-Alanine | 8.90 |
| L-Arginine - HCl | 126.00 |
| L-Asparagine - $H_2O$ | 15.00 |
| L-Aspartic Acid | 13.30 |
| L-Cystine - 2HCl | 31.28 |
| L-Glutamic Acid | 14.70 |
| Glycine | 292.00 |
| L-Histidine - HCl—$H_2O$ | 7.50 |
| L-Histidine | 42.00 |
| L-Isoleucine | 52.00 |
| L-Leucine | 52.00 |
| L-Lysine | 72.50 |
| L-Methionine | 15.00 |
| L-Phenylalanine | 32.00 |
| L-Proline | 11.50 |
| L-Serine | 10.50 |
| L-Threonine | 48.00 |
| L-Tryptophan | 10.00 |
| L-Tyrosine | 51.90 |
| L-Valine | 46.00 |
| D-Ca Pantothenate | 1.00 |
| Choline Chloride | 1.00 |
| Folic Acid | 1.00 |
| i-Inositol | 2.00 |
| Niacinamide | 1.00 |
| Pyroxidal HCl | 1.00 |
| Riboflavin | 0.10 |
| Thiamine HCl | 1.00 |

"Penicillin-Streptomycin Solution" is a preparation consisting of 5,000 μg/ml Penicillin G sodium and 5,000 μg/ml Streptomycin sulfate in 0.85% saline and is also available from Invitrogen.

PABs of the present invention have differing properties in terms of comparative levels of toxicity, antimicrobial activity, cellular proliferative activity and/or stimulatory activity (i.e., in terms of gene expression). As described below, some have low toxicity for mammalian cells and high toxicity for prokaryotic life forms, while others have the ability to increase metabolic soluble proteins. Still others have the ability to increase the synthesis and/or slow degradation of extracellular skin matrix proteins as well as the ability to increase proliferation of fibroblast cells.

As used in the present application, by the term "biosurfactant" is meant a molecule having a charged hydrophilic head and long-chain carbon hydrophobic tail, preferably from about 8 to 22 carbon atoms in length. These molecules are described as biosurfactants because they auto-aggregate above their critical micelle concentration into polymeric structures. In this respect, the compositions of the present invention may be distinguished from the "FLAK" peptides (i.e., those containing Phenylalanine, Leucine, Alanine, and Lysine residues) as described in U.S. Pat. No. 6,875,744 which do not auto-aggregate in solution.

As used in the present application, by the term "acid C-terminus" is meant the functional group —COOH.

As used in the present application, by the term "amide C-terminus" is meant a functional group selected from —CONH$_2$, —CONHR, —CONR$_2$ where R is an alkyl, aryl or alkyl-aryl moiety.

Acylation is a process well-known to those of skill in the art for protecting the N-terminus of an amino acid sequence to prevent further reactions with that group. Acyl functional groups have the formula R(C=O)—, where R is an organic group. They are formed by removal of the carboxylic hydroxyl group from an organic acid.

Methods for attaching acyl moieties at the N-terminus of an amino acid or amino acid sequence are well-known in the art. Among those known to those of skill in the art are the Friedel-Craft and Schotten-Baumann reactions, both using acyl chlorides. See e.g., U.S. Pat. No. 4,126,628, Japanese Patent No. JP 11140032, German Patent No. DE 19749556. See also Iyer, V. N., et al, *J. Indian Chem. Soc.* 59: 856-859 (1982); Paquet A. et al., Can. J. Chem. 60: 1806-1808 (1982).

Preferred acyl groups useful in the present invention have from 8 to 22 carbon atoms, branched or unbranched, saturated or unsaturated. More preferably, the acyl moiety is selected from the group consisting of myristoyl and palmitoyl.

One aspect of the present invention is directed to the following myristoylated PABs: SEQ ID NO: 1, SEQ ID NO: 2, SEQ ID NO: 4, SEQ ID NO: 5, SEQ ID NO: 7, SEQ ID NO: 9, SEQ ID NO: 10, SEQ ID NO: 12, SEQ ID NO: 15, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO:24, SEQ ID NO: 25, SEQ ID NO: 26, SEQ ID NO: 27, SEQ ID NO: 27, SEQ ID NO: 28, SEQ ID NO: 29, SEQ ID NO: 30, SEQ ID NO: 31, SEQ ID NO: 32 and SEQ ID NO: 33.

Another aspect of the present invention is directed to the following palmitoylated PABs: SEQ ID NO: 3, SEQ ID NO: 6, SEQ ID NO: 8, SEQ ID NO: 11, SEQ ID NO:13, SEQ ID NO: 14 and SEQ ID NO: 16.

For purposes of protecting the carboxy-terminal of the last amino acid of an amino acid sequence, one of the following protective groupings may be attached: —OR or —NHR, where R is selected from the group consisting of H or an alkyl group of up to 22 carbon atoms, branched or unbranched, saturated or unsaturated, linear or cyclic. These processes, esterification (—OR) and amidation (—NHR), are also well-known to persons of skill in the art.

One aspect of the present invention is directed to the following PABs having an amide C-terminus: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 9, SEQ ID NO: 10, SEQ ID NO: 12, SEQ ID NO: 13, SEQ ID NO: 15, SEQ ID NO: 17, SEQ ID NO: 19, SEQ ID NO: 21, SEQ ID NO: 22, SEQ ID NO: 23, SEQ ID NO: 26, SEQ ID NO: 27, SEQ ID NO: 27, SEQ ID NO: 28, SEQ ID NO: 29, SEQ ID NO: 30, SEQ ID NO: 32 and SEQ ID NO: 33.

Without wishing to be bound to a theory, Applicants believe that certain PABs having a carboxyamide group at the end of the amino acid sequence are preferred because they are less likely to be labile to acid hydrolysis of the N-terminal alkyl group, especially at pH values less than physiological pH. Further, certain amide-terminated PABs have been found to have a higher LD$_{50}$ for mammalian cells as well as a higher efficacy (as expressed in lower minimum inhibitory concentration) and/or broader range of antimicrobial activity.

Another aspect of the present invention is directed to the following PABs having an acid C-terminus: SEQ ID NO. 20, SEQ ID NO: 24, SEQ ID NO: 25 and SEQ ID NO: 31.

The number of charged amino acid residues in the PABs of the present invention is at least one, more preferably at least two. The presence of multiple charged amino acid residues confers desirable properties including in terms of antimicrobial activity. However, because of steric effects and other biological interactions, predicting antimicrobial activity (as well as other properties) based on number of charged amino acid residues has proven to be elusive.

One aspect of the present invention is directed to the following PABs in which the percentage of charged amino acid residues is at least about 33% of the total number of amino acid residues: SEQ ID NO: 1, SEQ ID NO: 2, SEQ ID NO: 3, SEQ ID NO: 4, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 27, SEQ ID NO: 28, SEQ ID NO: 29, SEQ ID NO: 30, SEQ ID NO: 31, SEQ ID NO: 32 and SEQ ID NO: 33.

Another aspect of the present invention is directed to the following PABs in which the percentage of charged amino acid residues is at least about 50% of the total number of amino acid residues: SEQ ID NO: 1, SEQ ID NO: 2, SEQ ID NO: 3, SEQ ID NO: 4, SEQ ID NO: 5, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 22, SEQ ID NO: 25, SEQ ID NO: 27, SEQ ID NO: 27, SEQ ID NO: 29, SEQ ID NO: 30, SEQ ID NO: 32 and SEQ ID NO: 33.

Yet another aspect of the present invention is directed to the following PABs in which the percentage of charged amino acid residues is at least about 60% of the total number of amino acid residues: SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 25, SEQ ID NO: 27, SEQ ID NO: 27 and SEQ ID NO: 30.

An additional aspect of the present invention is directed to the following PABs in which at least two of amino acid residues are charged: SEQ ID NO: 1, SEQ ID NO: 2, SEQ ID NO: 3, SEQ ID NO: 4, SEQ ID NO: 5, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 27, SEQ ID NO: 28, SEQ ID NO: 29, SEQ ID NO: 30, SEQ ID NO: 31, SEQ ID NO: 32 and SEQ ID NO: 33.

A further aspect of the present invention is directed to the following PABs in which at least three of amino acid residues are charged: SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 22, SEQ ID NO: 23, SEQ ID NO: 24, SEQ ID NO: 25, SEQ ID NO: 27, SEQ ID NO: 27, SEQ ID NO: 30 and SEQ ID NO: 31.

A still further aspect of the present invention is directed to the following PABs in which at least four of amino acid residues are charged: SEQ ID NO: 11, SEQ ID NO: 22 and SEQ ID NO: 27.

PABs of the present invention have surprisingly and unexpectedly low CMCs in an aqueous MEM environment—some at less than about 100 ppm, others at less than about 50 ppm, and still others at less than 25 ppm.

One aspect of the present invention is therefore directed to the following PABs which have a CMC of less than about 100 ppm in an aqueous MEM environment: SEQ ID NO: 1, SEQ ID NO: 2, SEQ ID NO: 3, SEQ ID NO: 4, SEQ ID NO: 5, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 27, SEQ ID NO: 28, SEQ ID NO: 29, SEQ ID NO: 30, SEQ ID NO: 31, SEQ ID NO: 32 and SEQ ID NO: 33.

Another aspect of the present invention is directed to the following PABs which have a CMC of less than about 50 ppm in an aqueous MEM environment: SEQ ID NO: 1, SEQ ID NO: 2, SEQ ID NO: 3, SEQ ID NO: 4, SEQ ID NO: 5, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 18, SEQ ID NO: 19, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 27, SEQ ID NO: 28, SEQ ID NO: 29, SEQ ID NO: 30, SEQ ID NO: 31, SEQ ID NO: 32 and SEQ ID NO: 33.

Yet another aspect of the present invention is directed to the following PABs which have a CMC of less than about 25 ppm in an aqueous MEM environment: SEQ ID NO: 1, SEQ ID NO: 3, SEQ ID NO: 4, SEQ ID NO: 5, SEQ ID NO: 8, SEQ ID NO: 9, SEQ ID NO: 11, SEQ ID NO: 12, SEQ ID NO: 13, SEQ ID NO: 14, SEQ ID NO: 15, SEQ ID NO: 16, SEQ ID NO: 18, SEQ ID NO: 19, SEQ ID NO: 21, SEQ ID NO: 23, SEQ ID NO: 24, SEQ ID NO: 25, SEQ ID NO: 29, SEQ ID NO: 30, SEQ ID NO: 31, SEQ ID NO: 32 and SEQ ID NO: 33.

One aspect of the present invention is directed to the following PABs which have an $LD_{50}$ of greater than about 200 ppm in cultured 37-year old female fibroblast cells (ATCC Reference—CRL-2122), preferably greater than about 500, where $LD_{50}$ is defined as the administered dose that results in the death of half or 50% of the test population of cells: SEQ ID NO: 1, SEQ ID NO: 2, SEQ ID NO: 7, SEQ ID NO: 8, SEQ ID NO: 9, SEQ ID NO: 10, SEQ ID NO: 15, SEQ ID NO: 18, SEQ ID NO: 19, SEQ ID NO: 20, SEQ ID NO: 21, SEQ ID NO: 22, SEQ ID NO: 24, SEQ ID NO: 25, SEQ ID NO: 26, SEQ ID NO: 27, SEQ ID NO: 28, SEQ ID NO: 29, SEQ ID NO: 30.

For purposes of the present invention, cytotoxicity to mammalian cells is determined using the CellTiter Blue Assay (Promega Corp., Madison, Wis.) in 37 year-old female fibroblast cells (ATCC CRL-2122). As will be appreciated by persons of skill in the art, other similar cytotoxicity assays, such as the Alamar Blue Assays available from Biosource International and Trek Diagnostic Systems, may also be used. The Promega assay is based on the indicator dye alamar blue (also known as resazurin), a redox indicator that produces a fluorescent colorimetric signal in response to cellular metabolic activity of cells. More particularly, the dye permeates both the cellular and nuclear membranes of cells and is metabolized both by mitochondria and cytoplasmic microsomes. When metabolized, the dye forms a fluorimetric species with an emission at 590 nm. By measuring the intensity of the fluorescence, cellular viability can be quantified.

Visible signs of aging (e.g., fine lines and wrinkles) are correlated with a decrease in fibroblast proliferation as well as levels of collagen and elastin in the skin. The latter may be attributable to one or both of two cellular processes—decreased synthesis of collagen and/or elastin and/or increased enzymatic degradation of these proteins by elastases and/or collagenases, in particular Collagenase I, also known as Matrix Metalloprotease 1 (MMP1). Surprisingly and unexpectedly, at a concentration less than the $LD_{50}$ PABs of the present invention cause an increase in metabolic soluble proteins (e.g., extracellular skin matrix proteins, such as collagen, elastin, fibronectin, as well as proteins involved in intercellular adhesion such as decorin, and scavenging of free radicals) of at least about 20%.

For purposes of the present invention, metabolic soluble protein is measured using the CBQCA Protein Quantitation Assay from Molecular Probes, Inc. (Eugene, Oreg.). This assay is based on a quinoline-2-carboxaldehyde derivative, which specifically reacts with primary amines to form conjugates capable of electrophoretic or chromatographic analysis. More specifically, in the presence of the cyanide anion, the quinoline-2-carboxaldehyde derivative reacts with primary amines, including those on proteins, and produces a highly-fluorescent emission at 550 nm.

One embodiment of this aspect of the present invention is directed to the following PABs which at a concentration less than the $LD_{50}$ cause an increase in metabolic soluble protein of at least about 20% as measured by CBQCA Assay: SEQ ID NO: 1, SEQ ID NO: 2, SEQ ID NO: 4, SEQ ID NO: 7, SEQ ID NO: 12, SEQ ID NO: 13, SEQ ID NO: 14, SEQ ID NO: 15, SEQ ID NO: 17, SEQ ID NO: 18, SEQ ID NO: 20, SEQ ID NO: 21, SEQ ID NO: 23, SEQ ID NO: 24, SEQ ID NO: 25, SEQ ID NO: 26, SEQ ID NO: 28, SEQ ID NO: 29, SEQ ID NO: 30, SEQ ID NO: 31, SEQ ID NO: 32 and SEQ ID NO: 33.

A preferred embodiment of this aspect of the present invention is directed to the following PABs which at a concentration less than the $LD_{50}$ cause an increase in metabolic soluble protein of at least about 30% as measured by CBQCA Assay: SEQ ID NO: 1, SEQ ID NO: 2, SEQ ID NO: 7, SEQ ID NO: 14, SEQ ID NO: 15, SEQ ID NO: 17, SEQ ID NO: 18, SEQ ID NO: 20, SEQ ID NO: 23, SEQ ID NO: 24, SEQ ID NO: 25, SEQ ID NO: 26, SEQ ID NO: 28, SEQ ID NO: 29, SEQ ID NO: 30 and SEQ ID NO: 31.

A particularly preferred embodiment of this aspect of the present invention is directed to the following PABs which at a concentration less than the $LD_{50}$ cause an increase in metabolic soluble protein of at least about 50% as measured by CBQCA Assay: SEQ ID NO: 1, SEQ ID NO: 2, SEQ ID NO: 7, SEQ ID NO: 14, SEQ ID NO: 15, SEQ ID NO: 17, SEQ ID NO: 18, SEQ ID NO: 20, SEQ ID NO: 23, SEQ ID NO: 24, SEQ ID NO: 25, SEQ ID NO: 26, SEQ ID NO: 28, SEQ ID NO: 29, SEQ ID NO: 30 and SEQ ID NO: 31.

PABs of the present invention have surprisingly and unexpectedly been found to causes an increase in the expression genes which code for three extracellular skin matrix proteins—COL1 (collagen), fibronectin (FN1) and elastin (ELN). Accordingly, another aspect of the present invention is directed to PABs that increase the expression of one or more genes that code for collagen, elastin or fibronectin. Levels of gene expression can be measured using DNA microarrays and a variety of other techniques well-known to those of skill in the art. See, e.g., Perou et al., Nature (London), 406: 747-752 (2000).

One embodiment of this aspect of the present invention is directed to the following PABs which at a concentration of 10 ppm cause an increase of at least twenty percent in the expression of at least two of ELN, FN1, or COL1: SEQ ID NO: 7, SEQ ID NO: 9, SEQ ID NO: 10, SEQ ID NO: 12, SEQ ID NO: 18, SEQ ID NO: 21, SEQ ID NO: 22, SEQ ID NO: 24, SEQ ID NO: 26 and SEQ ID NO: 27.

A more preferred embodiment of this aspect of the present invention is directed to the following PABs which at a concentration of 10 ppm cause an increase of at least twenty percent in the expression of ELN, FN1 and COL1: SEQ ID NO: 7, SEQ ID NO: 9, SEQ ID NO: 10, SEQ ID NO: 18, SEQ ID NO: 21, SEQ ID NO: 22, SEQ ID NO: 24 and SEQ ID NO: 27.

A still more preferred embodiment of this aspect of the invention is directed to the following PABs that at a concentration of 10 ppm not only cause at least a twenty percent increase in the expression of at least two of COL1, ELN or FN1 but also at the same time do not increase the expression of MMP1: SEQ ID NO: 7, SEQ ID NO: 9, SEQ ID NO: 10, SEQ ID NO: 12, SEQ ID NO: 18, SEQ ID NO: 21, SEQ ID NO: 24 and SEQ ID NO: 27.

An even more preferred embodiment of this aspect of the invention is directed to the following PABs that cause at least a twenty percent increase in the expression of at least two of COL1, ELN or FN1 and downregulate expression of MMP1 by at least twenty percent: SEQ ID NO: 7, SEQ ID NO: 9 and SEQ ID NO: 10.

Other negative sequelae are often associated surfactants. These can include undesired inflammatory responses, which can be manifested in increased expression of IL6 and IL8. PABs of the present invention have surprisingly and unexpectedly been found not to increase, and in some cases, to decrease the expression of IL6 and IL8.

One embodiment of this aspect of the present invention is directed to the following PABs that cause a twenty percent increase in the expression of at least two of COL1, ELN or FN1 while at the same time not increasing expression of IL6 and IL8: SEQ ID NO: 7, SEQ ID NO: 9, SEQ ID NO: 12, SEQ ID NO: 18, SEQ ID NO: 21, SEQ ID NO: 22, SEQ ID NO: 24 and SEQ ID NO: 26.

A further and more preferred embodiment of this aspect of the present invention is directed to the following PABs that cause (i) at least a twenty percent increase in the expression of at least two of COL1, ELN or FN1 and (ii) at least a twenty percent decrease in the expression of at least one of IL6 or IL8 while at the same time (iii) not causing an increase in IL6 or IL8: SEQ ID NO: 7, SEQ ID NO: 9, SEQ ID NO: 12, SEQ ID NO: 18, SEQ ID NO: 21, SEQ ID NO: 24 and SEQ ID NO: 26.

A still further and even more preferred aspect of the present invention is directed to the following PABs that cause (i) at least a twenty percent increase in the expression of at least two of COL1, ELN or FN1 and (ii) at least a twenty percent decrease in the expression of at least IL6 and IL8: SEQ ID NO: 7, SEQ ID NO: 9, SEQ ID NO: 12, SEQ ID NO: 18, and SEQ ID NO: 21.

A particularly preferred embodiment of this aspect of the present invention is directed to the following PABs that at a concentration of 10 ppm cause an increase of at least twenty percent in the expression of at least two of ELN, FN1, or COL1 and does not cause an increase in the expression of MMP1, IL6 or IL8: SEQ ID NO: 7, SEQ ID NO: 9, SEQ ID NO: 12, SEQ ID NO: 18, SEQ ID NO: 21 and SEQ ID NO: 24.

Chronic upregulation of inflammatory genes (e.g., IL6 and IL8) has been observed to be correlated with upregulation of apoptotic genes such as CASP 1. The significant up-regulation of the pro-inflammatory genes IL-6 and IL-8 and/or the apoptotic related genes such as caspase 1 (CASP1) is not desirable. Lyer, V. R. et al., Science 283: 83-87 (1999); Mathy-Hartert M at al., Inflamm Res. 52(3):111-8 (2003); Raqib et al., Infection and Immunity June 2002, pp 3199-3207. Accordingly, another aspect of the present invention is directed to PABs which do not cause an increase in expression of CASP1.

One embodiment of this aspect of the invention is directed to the following PABs which at a concentration of 10 ppm do not cause an increase in the expression of CASP1: SEQ ID NO: 7, SEQ ID NO: 9, SEQ ID NO: 10, SEQ ID NO: 18, and SEQ ID NO: 21.

A preferred embodiment of this aspect of the invention is directed to the following PABs which at a concentration of 10 ppm cause a decrease in the expression of CASP1: SEQ ID NO: 7 and SEQ ID NO: 10.

Another aspect of the present invention is directed to PABs that increase fibroblast proliferation. For purposes of the present invention, proliferation is assessed using the Cyquant® Cell Proliferation Assay from Molecular Probes. This assay measures increased production of cellular nucleic acids which in turn results in increased binding of fluorescent dye.

One embodiment of this aspect of the present invention is directed to the following PABs which after a period of 24 hours at a concentration of 1 ppm cause an increase in fibroblast proliferation of at least about twenty percent: SEQ ID NO: 4, SEQ ID NO: 8, SEQ ID NO: 9 and SEQ ID NO: 17.

Another embodiment of this aspect of the present invention is directed to the following PABs which after a period of 24 hours at a concentration of 10 ppm cause an increase in fibroblast proliferation of at least about twenty percent: SEQ ID NO: 3, SEQ ID NO: 7, SEQ ID NO: 11, SEQ ID NO: 13, SEQ ID NO: 14, SEQ ID NO: 15, SEQ ID NO: 16, SEQ ID NO: 20, and SEQ ID NO: 32.

Yet another embodiment of this aspect of the present invention is directed to the following PABs which after a period of 48 hours at a concentration of 10 ppm cause an increase in fibroblast proliferation of at least about twenty percent: SEQ ID NO: 19, SEQ ID NO: 24 and SEQ ID NO: 25.

A still further embodiment of this aspect of the present invention is directed to the following PABs which after a period of 48 hours at a concentration of 25 ppm cause an increase in fibroblast proliferation of at least about twenty percent: SEQ ID NO: 12 and SEQ ID NO: 23.

The ability of PABs of the present invention to effectively wet surfaces at low CMCs confers another surprising and unexpected property—broad spectrum antimicrobial activity. By "antimicrobial" activity is meant the ability to inhibit the growth of at least one microbial organism selected from the group consisting E. coli, P. aeruginosa, S. aureus and C. albicans, as confirmed by optical density measurement ("OD").

By "inhibition of growth" is meant reduction or absence of an increase greater than 5% in OD, a dimensionless measure of turbidity that is proportional to the amount of microbial cells present in a sample. For illustrative purposes, a PAB according to the present invention is added to a culture plate on which E. coli is present at a final concentration of about $5\times10^3$ cfu/ml. The plate is then incubated at about 37° C. for about 24 hours at which time the E. coli is resuspended by shaking, and OD is measured at about 600 nm. Thus, a reduction or absence of an increase greater than 5% in OD confirms the antimicrobial nature of the PAB with respect to E. coli.

One embodiment of this aspect of the present invention is directed to the following PABs which inhibit the growth of E. coli at a concentration of 100 ppm or less, as confirmed by OD measurements: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 27, SEQ ID NO: 28, SEQ ID NO: 29, SEQ ID NO: 30, SEQ ID NO: 31, SEQ ID NO: 32 and SEQ ID NO: 33.

A preferred embodiment of this aspect of the present invention is directed to the following PABs which at a concentration of 100 ppm or less inhibit the growth of E. coli and P. aeruginosa or S. aureus: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 27, SEQ ID NO: 29, SEQ ID NO: 30, SEQ ID NO: 31, SEQ ID NO: 32 and SEQ ID NO: 33.

A more preferred embodiment of this aspect of the invention is directed to the following PABs which at a concentration of 100 ppm or less inhibit the growth of E. coli, C. albicans and P. aeruginosa or S. aureus: SEQ ID NO: 1, SEQ ID NO: 2, SEQ ID NO: 5, SEQ ID NO: 7, SEQ ID NO: 12, SEQ ID NO: 15, SEQ ID NO: 18, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 31, and SEQ ID NO: 33.

A still more preferred embodiment of this aspect of the invention is directed to the following PABs which at a concentration of less than or equal to about 100 ppm inhibit the growth of E. coli, P. aeruginosa, S. aureus and C. albicans: SEQ ID NO: 1, SEQ ID NO: 2, SEQ ID NO: 7, SEQ ID NO: 12, SEQ ID NO: 15, SEQ ID NO: 18, SEQ ID NO: 23, SEQ ID NO: 24, SEQ ID NO: 25, SEQ ID NO: 31 and SEQ ID NO: 33.

An even more preferred embodiment of this aspect of the invention is directed to the following PABs which at a concentration of 25 ppm inhibits the growth of E. coli, P. aeruginosa, S. aureus and Methicillin-resistant Staphylococcus aureus ("MRSA"): SEQ ID NO: 12, SEQ ID NO: 15, SEQ ID NO: 30 and SEQ ID NO: 31. By MRSA is meant isolates of the bacterium S. aureus that have acquired genes encoding resistance to the antibiotic methicillin.

Based on the unexpected and surprising properties described above, PABs of the present invention may be used in topical therapeutic applications, including helping to reduce the appearance of signs of aging. These are discussed below. As will be appreciated by those of skill in the art, in this context of therapeutic agents, it is important to balance potential efficacy against toxicity. Another aspect of the present invention is therefore directed to PABs having a favorable toxicity-to-therapeutic ratio ("TTR"). For purposes of the present application, the TTR for a PAB is expressed as terms of the ratio of $LD_{50}$ to the minimum inhibitory concentration (MIC) of the PAB for E. coli, expressed as $LD_{50}/MIC_{(E.\ coli)}$.

As discussed above, assessing the antimicrobial activity of a compound using the MIC is a method well-known to those of skill in the art. A compound to be tested is serially diluted into growth medium, inoculated with culture and then incubated. The MIC is the lowest dilution of compound that inhibits or prevents growth of the target microorganism.

The relative toxicity of a PAB is not predictable and can be influenced by the choice of acyl group at the N-terminus, the sequence and spacing of charged amino acid moieties and whether a protecting amide group is attached at the C-terminus. This is illustrated below.

Pal-GHK amide and Pal-GHR amide [P250] are both monocationic tripeptides with identical acyl and amide protecting groups. Changing the positively charged amino acid residue in the last amino acid position from Lysine to Arginine increases the $LD_{50}$ four-fold from 35 to 140. The disparity in $MIC_{(E.\ coli)}$ for these two compounds differs by 25-fold: 250 ppm for Pal-GHK amide versus 10 ppm for Pal-GHR amide. The TTR for Pal-GHR amide is thus 140-fold more favorable than Pal-GHK amide (14 versus 0.1).

Comparison of Myr-KKALK amide (SEQ ID NO: 12) and Myr-KLAKK amide (SEQ ID NO: 7) illustrates the unpredictable significantly different properties that can result from varying the sequence of even the same amino acid residues. Both are acylated, amide-terminated tricationic oligopeptides with one monolysinyl and one dilysinyl group. Both have a $MIC_{(E.\ coli)}$ of 10 ppm. However, SEQ ID NO: 7 has an $LD_{50}$ of 500, whereas SEQ ID NO: 12 has an $LD_{50}$ of 135.

Inserting a non-charged amino acid at the end of the same charged amino acid sequence, and not protecting the last non-charged amino acid (i.e., by amidation) can likewise have a profound effect on MIC. For example, surprisingly and unexpectedly, Myr-KLAKK amide (SEQ ID NO: 7) has $MIC_{(E.\ coli)}$ of 10 ppm. Myr-KLAKKL acid (SEQ ID NO: 18) has a $MIC_{(E.\ coli)}$ five-fold higher at 50 ppm.

The marked difference between acid and amide termination of the same amino acid sequence is illustrated by the Pal-KTTKS sequence. Whereas the amide-terminated sequence has a $MIC_{(E.\ coli)}$ of 10 ppm, the non-protected (i.e., acid-terminated) sequence has a $MIC_{(E.\ coli)}$ of greater than 500 ppm.

This comparison also illustrates differences in effect of stimulatory and proliferative effects of acylated amino acid sequences. For example, at 10 ppm concentration, Pal-KTTKS acid does not significantly increase metabolic soluble proteins or significantly stimulate cell proliferation at or near its CMC.

Acylation of a peptide moiety can change the MIC by as much as twenty-fold. For example, $MIC_{(E.\ coli)}$ for STKTTK amide is >500 ppm. Additionally, as discussed above, this non-acylated sequence has no CMC and is therefore not a PAB within the scope of the present invention. Attaching a myristoyl group to the N-terminus of this amino acid sequence—and creating a PAB within the scope of the invention—lowers $MIC_{(E.\ coli)}$ to 25 ppm. This translates into a more than twenty-fold difference in TTR—with Myr-STKTTK amide (SEQ ID NO: 21) having a TTR twenty times more favorable than STKTTK amide (>40 versus 2.)

One embodiment of this aspect of the present invention is directed the PABs having a TTR of greater than 10 and selected from the group consisting of SEQ ID NO: 1, SEQ ID NO: 2, SEQ ID NO: 7, SEQ ID NO: 8, SEQ ID NO: 10, SEQ ID NO: 12, SEQ ID NO: 14, SEQ ID NO: 15, SEQ ID NO: 18, SEQ ID NO: 19, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, and SEQ ID NO: 30.

More preferred embodiments of this aspect of the invention are directed to the following PABs having a TTR of greater than ten which at a concentration of 10 ppm cause an increase in the expression of at least two of ELN, FN1 and COL1: SEQ ID NO: 7, SEQ ID NO: 10, SEQ ID NO: 12, SEQ ID NO: 18, SEQ ID NO: 21, SEQ ID NO: 22, SEQ ID NO: 24, SEQ ID NO: 26 and SEQ ID NO: 27.

Even more preferred embodiments of this aspect of the invention are directed to the following PABs having a TTR of greater than ten which at a concentration of 10 ppm cause a twenty percent increase in the expression of at least two of ELN, FN1 and COL1 but do not cause an increase in the expression of MMP1, IL6 or IL8: SEQ ID NO: 7, SEQ ID NO: 12, SEQ ID NO: 18, SEQ ID NO: 21 and SEQ ID NO: 24.

Still other preferred embodiments of this aspect of the invention are directed to the following PABs having a TTR of greater than twenty that also cause an increase in the expression of at least two of ELN, FN1 and COL1: SEQ ID NO: 7, SEQ ID NO: 12, SEQ ID NO: 18, SEQ ID NO: 22 and SEQ ID NO: 24.

One aspect of the present invention is directed to topical therapeutic application of PABs to treat dermatologic conditions, particularly helping to reduce the appearance of signs of aging. Additionally, treatment with PABs within the scope of the present invention may reduce or prevent undesired inflammatory responses often associated with topical dermatologic therapies. Compositions of the present invention may also be used in the practice of dermatology. Non-limiting examples of conditions that may be improved or maintained by using one or more PABs within the scope of the present invention are: skin elasticity; skin firmness; skin moisture; skin dryness; pruritus; blotches; fine lines and wrinkles; lentigines; age spots; acne; hyperpigmented skin; keratoses; rosacea; inflammatory dermatoses; skin atrophy; wound healing. Additionally, as described above, compositions of the present invention may be used in the treatment of microbial infections as well as conditions described in Kerdel, et al., *Dermatologic Therapeutics* (2005), and in Hardman et al., *Goodman & Gilman's: The Pharmacological Basis of Therapeutics* (10$^{th}$ Edition, 2001).

The CTFA Dictionary describes a wide variety of non-limiting cosmetic and pharmaceutical ingredients that, optionally, are suitable for use in formulations containing PABs according to the present invention. Examples of these ingredient classes include: abrasives, exfoliants, absorbents, astringents, antimicrobial agents, preservatives, antioxidants, anti-inflammatory agents, vitamins, trace minerals, film formers and other polymeric materials that increase the substantivity of topical compositions to the skin, humectants, moisturizers, pH adjusters, skin-conditioning agents, skin soothing and/or healing agents, anti-acne agents, skin bleaching and lightening agents, external analgesics, sunscreen actives (i.e., organic compounds that absorb ultraviolet radiation from 290 nm to 400 nm, inorganic compounds that scatter or block ultraviolet radiation). Other examples of cosmetic and/or pharmaceutical ingredients which are suitable for use in the delivery system of the present invention are disclosed in U.S. Pat. Nos. 6,492,326 and 6,974,799 and U.S. Patent Application Publication No. 2005/0142095, the disclosures of which are incorporated herein by reference.

The amino acid sequences of the present invention can be made synthetically by techniques well-known to those of skill in the art, including solid state peptide synthesis as described, for example, in U.S. Pat. No. 6,620,419.

EXAMPLES

The following examples are further illustrative of the present invention. The components and specific ingredients are presented as being typical, and various modifications can be derived in view of the foregoing disclosure within the scope of the invention. Unless otherwise noted, percentages are by weight of the total composition.

Example 1

Gel

| | |
|---|---|
| 1. DI Water | 95-98% |
| 2. Xanthan gum | 0.1-0.3% |
| 3. Magnesium ascorbyl phosphate | 1-3% |
| 4. Polymeric Acylated Biosurfactant SEQ ID NO 12* | 10-1000 ppm |
| 5. Sodium Hydroxymethylglycinate** | 0.3-1% |

*From Therapeutic Peptides Inc. (Harahan, LA)
**Suttocide A from Sutton Labs (Chatham, NJ)

Add Ingredients 2-5 to DI Water (#1) while mixing at 1,000 rpm in a Silverson mixer until homogenous.

Example 2

Cream/Lotion

| Phase A | |
|---|---|
| Cyclopentasiloxane* | 20-30% |
| Cyclopentasiloxane (and) PEG-12 Dimethicone Crosspolymer** | 7-15% |
| Cyclopentasiloxane (and) Dimethicone Crosspolymer (and) Dimethicone/Vinyl Dimethicone Crosspolymer*** | 7-15% |
| Phase B | |
| DI water | QS |
| Polysorbate 20 | 0.1-1% |
| Dipropylene glycol, Propylene glycol, Glycerol, Butylene glycol | 20-30% |
| Magnesium ascorbyl phosphate | 1-3% |
| Minimal Essential Media | 1-5% |
| Polymeric Acylated Biosurfactant SEQ ID NO: 21**** | 10-1000 ppm |
| Methyl paraben, Butylparaben | 0.2-1% |

*Dow Corning 245 Fluid
**Dow Corning 9011 Silicone Elastomer Blend
***Dow Corning 9546 Silicone Elastomer Blend
****From Therapeutic Peptides Inc. (Harahan, LA)

Add Phase A to Phase B while mixing at 1,000 rpm in a Silverson mixer until homogenous.

Example 3

Nanoparticulate Concentrate

| Phase A | |
|---|---|
| DI Water | 70-90% |
| Phase B | |
| Medium chain triglyceride ($C_6$-$C_{12}$) | 2-8% |
| Lecithin | 2-8% |
| Medium chain fatty acid ($C_6$-$C_{12}$) | 2-8% |
| Lysine or arginine | 1-2% |
| Polymeric Acylated Biosurfactant SEQ ID NO 21* | 10-1000 ppm |

*From Therapeutic Peptides Inc. (Harahan, LA)

Mix Phase B into Phase A with a high speed homogenizer at 10,000-12,000 rpm at 30-40° C. for about 10 minutes. The resulting mixture is then processed in a colloid mill at greater than about 10,000 psi to produce particles sizes of less than about 200 nm. The resulting concentrate is added to a conventional macroemulsion cream at a concentration of from about 1 to about 20%.

Example 4

Improvement in Signs of Aging

The efficacy of topical compositions comprising therapeutically effective amounts of polymeric acylated biosurfactants of the present invention in reducing the signs of aging is measurable by reduction in the severity of superficial lines in the "Crow's Feet" area; by clinical assessment of skin texture and tone, and by self-assessment. In addition to these improvements in appearance, improvements in biophysical parameters, including skin tautness and elasticity, are measurable with a Twistometer.

Twenty adult female Caucasian subjects, ranging in age from mid-thirties to late-sixties, are enrolled in a Study. They are selected for mild to moderate photodamage, as specified in the Protocol. The subjects are clinically assessed at each Study visit, by the Principal Investigator, or by the Research Associate. Superficial facial lines (SFL) in the "Crow's Feet" (periorbital) area are assessed by the method of Packman and Gans. Packman, E. W., and Gans, E. H, "Topical moisturizers: quantification of their effect on superficial facial lines" *J. Soc. Cosmet. Chem.*, 29: 1-11 (1978). Briefly, the SFL score is a weighted sum of the numbers of lines/wrinkles of three classes, of increasing severity; shallow (n×1), definite (n×2), and deep (n×3). Severity of the flaws grouped in Skin Surface Texture and Tone (Table 3) are scored with a 0-10 analog scale.

Color photographs are taken with a Nikon D70 digital camera, under standardized conditions, with the camera mounted on a focusing stage, to assure that the reproduction ratio (magnification) is the same each time. Black and white photos are taken similarly, with a Nikon F-100 film camera, using T-max 100 print film, and using a UVA filter on the camera lens.

At the end of the eight week study, expert graders assess overall improvement in appearance from Baseline, using the color photographs. Assessment of changes in individual skin characteristics show that with treatment using compositions comprising biosurfactants of the present invention, the skin becomes smoother and less lined, pores are less evident, and skin color becomes more uniform. These changes are also perceptible to subjects in self-assessment.

Skin tautness and elasticity are measured with a Twistometer, of the type described by Finlay. Finlay, J. B. "The torsional characteristics of human skin in vivo." *Biomed. Eng.* 6: 567-573 (1971). Torsional stretch and rebound are measured, with a disc attached to the skin surface with adhesive tape, and rotated by a small electrical current which is held constant for a fixed period of time. The angle through which the attached disc can rotate is inversely related to skin tautness, and the elasticity of the twisted skin is directly related to the extent of the rebound when the current is turned off. Thus, a decrease in the torsional stretch indicates the skin has become more taut (firm), and an increase in the rebound that it has become more elastic:

Except for Twistometer measurements, non-parametric tests are used (Wilcoxon's Signed Ranks Test, or the 50% Probability Test) for assessing the statistical significance of changes in skin condition. These tests require no assumption of normal distribution, and are appropriate for analysis of scoring done with an ordinal or nominal scale, or for "yes or no" answers. For instrumental measurements, a paired difference "t-test" analysis for comparing "before" and "after" scores on the same subjects is used.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth hereinabove but rather that the claims be construed as encompassing all the features of patentable novelty which reside in the present invention, including all features which would be treated as equivalents thereof by those skilled in the art to which the invention pertains.

The invention claimed is:

1. A polymeric acylated biosurfactant conforming to the formula Acyl-AA-Term, wherein Acyl is an 8- to 22-membered carbon chain, branched or unbranched, saturated or unsaturated, wherein AA is a consecutive sequence of four to nine amino acid residues, wherein at least two of the amino acid residues are charged, wherein Term is an acid C-terminus or an amide C-terminus, and wherein the polymeric acylated biosurfactant is selected from the group consisting of SEQ ID NO: 3 (Pal-GRKG amide); SEQ ID NO: 4 (Myr-GRKG amide); SEQ ID NO: 9 (Myr-KKGEM amide); SEQ ID NO: 10 (Myr-KRGKP amide); SEQ ID NO: 11 (Pal-KRGDR acid); SEQ ID NO: 16 (Pal-GRKGD acid); SEQ ID NO: 17 (Myr-GRKGD amide); and SEQ ID NO: 27 (Myr-KRGDR amide).

2. A topically-applied cosmetic or dermatologic composition comprising (i) a polymeric acylated biosurfactant according to claim 1.

3. A topically-applied cosmetic or dermatologic composition of claim 2 in the form of a cream, lotion, gel or serum wherein the composition is a water-in-oil emulsion, an oil-in-water emulsion, a water-in-silicone emulsion, a silicone-in-water emulsion, a water-in-oil-in-water emulsion or an oil-in-water-in-oil emulsion.

4. A topically-applied cosmetic or dermatologic composition of claim 2 in the form of an anhydrous gel, serum, or a thickened aqueous dispersion.

5. A topically-applied cosmetic or dermatologic composition of claim 2 further comprising one or more cosmetic or pharmaceutical ingredients selected from the group consisting of abrasives, exfoliants, absorbents, astringents, antimicrobial agents, preservatives, antioxidants, anti-inflammatory agents, vitamins, trace minerals, film formers and other polymeric materials that increase the substantivity of topical compositions to the skin, humectants, moisturizers, pH adjusters, skin-conditioning agents, skin soothing and/or healing agents, anti-acne agents, skin bleaching and lightening agents, external analgesics, and sunscreen actives.

6. A polymeric acylated biosurfactant of claim 1 wherein after a period of 24 hours at a concentration of 1 ppm to 10 ppm the polymeric acylated biosurfactant causes an increase in fibroblast proliferation of at least about twenty percent and is selected from the group consisting of SEQ ID NO: 3 (Pal-GRKG amide), SEQ ID NO: 4 (Myr-GRKG amide), SEQ ID NO: 9 (Myr-KKGEM amide), SEQ ID NO: 11 (Pal-KRGDR acid), SEQ ID NO: 16 (Pal-GRKGD acid), and SEQ ID NO: 17 (Myr-GRKGD amide).

7. A polymeric acylated biosurfactant according to claim 1 wherein the polymeric acylated biosurfactant at a concentration of less than or equal to about 100 ppm inhibits the growth of *E. coli* and *P. aeruginosa* and is selected from the group consisting of SEQ ID NO: 4 (Myr-GRKG amide), SEQ ID NO: 9 (Myr-KKGEM amide), SEQ ID NO: 10 (Myr-KRGKP amide), SEQ ID NO: 11 (Pal-KRGDR acid), and SEQ ID NO: 17 (Myr-GRKGD amide).

* * * * *